(12) United States Patent
Fallin et al.

(10) Patent No.: US 7,090,677 B2
(45) Date of Patent: Aug. 15, 2006

(54) SURGICAL MILLING INSTRUMENT FOR SHAPING A BONE CAVITY

(75) Inventors: T. Wade Fallin, Hyde Park, UT (US);
 Daniel E. Gerbec, Logan, UT (US);
 John R. Pepper, Cheshire, CT (US)

(73) Assignee: Medicine Lodge, Inc., Logan, UT (US)

( * ) Notice: Subject to any disclaimer, the term of this patent is extended or adjusted under 35 U.S.C. 154(b) by 577 days.

(21) Appl. No.: 10/366,300

(22) Filed: Feb. 12, 2003

(65) Prior Publication Data

US 2003/0171756 A1 Sep. 11, 2003

Related U.S. Application Data

(60) Provisional application No. 60/356,945, filed on Feb. 12, 2002.

(51) Int. Cl.
 *A61B 17/00* (2006.01)
 *A61F 5/00* (2006.01)
(52) U.S. Cl. ..................................... 606/80
(58) Field of Classification Search ................ 606/79, 606/80, 86–88, 96
 See application file for complete search history.

(56) References Cited

U.S. PATENT DOCUMENTS

| | | | |
|---|---|---|---|
| 4,306,550 A | 12/1981 | Forte | |
| 4,466,429 A | 8/1984 | Loscher | |
| 4,777,942 A | 10/1988 | Frey | |
| 5,047,033 A | 9/1991 | Fallin | |
| 5,342,363 A * | 8/1994 | Richelsoph | 606/79 |
| 5,387,218 A | 2/1995 | Meswania | |
| 5,403,320 A | 4/1995 | Luman | |
| 5,496,324 A * | 3/1996 | Barnes | 606/79 |
| 5,527,316 A | 6/1996 | Stone | |
| 5,534,005 A | 7/1996 | Tokish | |
| 5,540,694 A | 7/1996 | DeCarlo | |
| 5,571,106 A | 11/1996 | Coufal | |
| 5,704,940 A | 1/1998 | Garosi | |
| 5,776,136 A | 7/1998 | Sahay | |
| 5,931,841 A | 8/1999 | Ralph | |
| 5,957,925 A | 9/1999 | Cook | |
| 5,976,145 A | 11/1999 | Kennefick | |
| 5,993,455 A | 11/1999 | Noble | |
| 6,045,556 A | 4/2000 | Cohen | |
| 6,283,970 B1 | 9/2001 | Lubinus | |

\* cited by examiner

*Primary Examiner*—Eduardo C. Robert
*Assistant Examiner*—Michael J. Araj
(74) *Attorney, Agent, or Firm*—David W. Meibos; Daniel F. Justin

(57) ABSTRACT

A mill guide instrument for guiding a tissue cutting tool is provided that is made up of subassemblies of a guide body and a mill guide. The guide body has a distal section dimensioned to fit into a bore in bone and a removable template with a guide surface unique to a proposed cavity shape. The mill guide is connected to the guide body and provides for controlled relative motion between the mill and the guide body. The mill guide has an attached stylus that follows the guide surface of the template. The stylus follows the template guide surface so as to constrain the path of the mill to a preferred milling path.

20 Claims, 17 Drawing Sheets

SURGICAL MILLING INSTRUMENT FOR SHAPING A BONE CAVITY

CROSS-REFERENCE TO RELATED APPLICATIONS

This patent application claims benefit of pending prior U.S. Provisional Patent Application Ser. No. 60/356,945, filed Feb. 12, 2002 by T. Wade Fallin et al. for SURGICAL MILLING INSTRUMENT FOR SHAPING A BONE CAVITY, which patent application is hereby incorporated herein by reference.

BACKGROUND OF THE INVENTION

As the external shapes of orthopedic surgical implants become more complex,-correspondingly sophisticated instruments are needed to prepare bone tissue to receive these implants. One such example are the instruments required to prepare the proximal femur for a total hip arthroplasty (THA) prosthesis. Other implant procedures such as total knee arthroplasty and total shoulder arthroplasty also require similar tissue preparation with milling instruments that replicate the three-dimensional geometry of the prosthesis surface.

The majority of THA implants in use today consist of three main components: the acetabular cup prosthesis, the femoral head prosthesis, and the femoral stem prosthesis. The acetabular cup prosthesis replaces the bearing cartilage in the acetabular hip socket of the pelvis. The femoral head prosthesis is a metal or ceramic ball that articulates in the acetabular cup prosthesis. It replaces the proximal spherical femoral head and the associated articular cartilage. The femoral prosthesis is typically a metal prosthesis implanted in the medullary canal of the femur. It connects the femur bone to the femoral head prosthesis and distributes the major hip loads from the acetabular socket to the femoral medullary canal.

A variety of geometrically complex femoral prosthesis designs have been developed. Originally these implants were available in a finite range of sizes and shapes. However, due to the range of anatomic variability between patients, a large inventory of implants was needed from which the surgeon would choose the best fitting prosthesis. As is inevitable with a finite selection of sizes to fit the infinitely variable anatomic structures of the human skeletal system, surgeons were typically forced to compromise their fit by selecting a prosthesis size that was either too large or too small or simply did not have the right shape to fit the patient optimally.

Consequently, modular femoral prosthesis systems have since been developed to both limit the number of parts in inventory and to also allow more intraoperative surgical sizing options. These modular systems allow the surgeon to build a prosthesis at the time of surgery that optimizes the shape of the implant to best match the unique anatomic requirements of a particular patient's proximal femur.

An assembled modular femoral prosthesis typically consists of three basic components: the proximal neck, the central body and the distal stem. A femoral prosthesis kit, available at the time of surgery, contains a range of sizes and shapes of each of these three components. Additionally, to accommodate more anatomic shaping options, these sections can be rotated at adjustable angles during assembly to optimize the shape of the final implant construct.

Although selecting the best prosthesis for a patient is critical to the success of a THA surgery, it is equally important to prepare the bone cavity to optimally fit the prosthesis. Long-term post surgical follow-up on patients has shown that the success of THA surgery is significantly influenced by the surgeon's ability to optimize the fit between the surgically prepared bone cavity and the load-bearing surface of the femoral prosthesis.

Ideally, the shape of the cavity should exactly match the shape of the external surface of the femoral prosthesis. This would allow an even distribution of the implant loads to the femoral bone, helping to prevent micro-motion between the prosthesis and the tissue. Since this micro-motion could eventually lead to loosening of the prosthesis, resulting in pain, instability and ultimately failure of the fixation, it is important to create the bone cavity so that it closely matches the implant.

Optimizing the cavity shape not only allows favorable load distribution between the prosthesis and the femur but also allows favorable tissue-to-implant apposition, so that there is more surface area contact for potential bone in-growth into the prosthesis. In the case of a non-cemented THA, this tissue-to-implant apposition allows bone tissue to eventually grow into the textured, bone in-growth surface on the prosthesis that is designed to mimic the cellular morphology of the inside of femoral bone.

Due to the variety of implant shapes that can be constructed with modular femoral prostheses, and the complexity of the anatomy of the proximal femur, it is generally not practical to precisely prepare a cavity to accept the prosthesis with conventional bone removal instrumentation. Typically, with conventional bone removal instrumentation, compromises in the shape of the cavity must be made that limit the surface area contact to allow for reasonable implant fit. At a minimum, contact in the anterior and posterior cortices, the medial cortex below the lesser trochanter, or the lateral cortex above the distal tip of the prosthesis is essential for good implant fixation. However, only contacting the implant in this area may result in a compromised fixation, unable to adequately prevent excessive relative micro-motion over the life of the implant.

The bone cavity is typically created freehand by incrementally removing small amounts of tissue with instruments such as drills, reamers, raps, and broaches. Then the surgeon intermittently tests the fit between implant and bone by inserting and removing the prosthesis and manually sculpting the cavity until the fit seems acceptable.

Another approach is to insert a reaming instrument, such as a long conical reamer or medullary drill, into the medullary cavity of the proximal femur. Then the bulk of the material in the calcar region is removed with a series of angled drills. This technique works for implants with a simple geometry, but does not work well for those with more complex curved surfaces.

Yet another approach is to use a series of broaches, each sequentially larger than the previous, that approximate the shape of the femoral prosthesis. Once the general size of the cavity is formed, the surgeon customizes it to best match the modular prosthesis geometry.

Such conventional bone removal techniques are typically not adequate to prepare the cavity for the more complex geometries associated with modular prostheses. The removal of too much tissue results in a mating surface with gaps that do not allow bone-to-implant apposition. The removal of too little tissue results in an improperly seated implant.

The texture of the cutting surface left by a bone removal instrument is also important to the long-term success of the procedure. When bone removal instruments such as broaches are used to remove relatively bulky segments of bone tissue, the resulting surface texture of the cavity is often too course for intimate implant-to-bone contact. The implant contacts the small rises between the cutting paths, leaving gaps between each area of contact.

SUMMARY OF THE INVENTION

Embodiments of this invention provide a bone milling instrument that is capable of accurately and precisely milling complex three-dimensional surfaces. This is accomplished by providing the surgeon with a bone milling instrument that guides a milling tool along a path predetermined by a template that is specific to a prosthesis geometry. The milling tool removes the bone tissue necessary to provide an optimal fit between the bone and the implant.

Embodiments of this invention provide a milling instrument that allows the surgeon to prepare a cavity that will mate with the external geometry a customized modular prosthesis. This is done by providing a series of interchangeable adjustable templates designed to guide the cutting instrument in a path that relates to the shape of a particular modular femoral prosthesis construct.

During an orthopedic procedure, surgeons need to see where their instruments are cutting tissue. Hence, embodiments of this invention provide instrumentation that does not obstruct the surgeon's view of the area where the bone-cutting instrument makes contact with the bone as the cavity is being milled. This is accomplished by moving the bulk of the instrumentation out of the surgeon's line of sight.

As implants, instrumentation and surgical techniques improve, the size of the incision and the invasiveness of the procedure necessary to accomplish a THA lessens. Hence, embodiments of this invention provide instrumentation that can be adapted for use in minimally invasive THA surgery. This is accomplished by providing minimally sized instruments that function through a minimally invasive incision and by providing instrumentation that is designed to only cut the tissue necessary for optimal cavity preparation.

The ideal bone cavity would be prepared by efficient bone removal tools such as milling cutters that would leave a textured mating surface more closely replicating that of the relatively smooth modular implant surface. This invention provides means for preparing the bone cavity with tools that leave a desired mating surface.

These and other embodiments are addressed by the provision and use of the present invention, which comprises a milling instrument for guiding a tissue cutting tool. The milling instrument is particularly helpful in preparing a cavity in bone to mate with a femoral prosthesis. The milling instrument comprises a guide body and a mill guide that help to guide a bone cutting instrument such as a mill.

The guide body has a distal section dimensioned to fit into a bore in bone. Templates, which are unique to the proposed cavity shape, are attached to the guide body. Three-dimensional and two-dimensional guide surfaces on the templates help guide the mill in the desired path to cut a cavity in the bone that is unique to the template guide surface shape.

Three milling instrument assembly embodiments are presented that allow the mill to follow complex three-dimensional cutting paths. These three embodiments of the invention use three-dimensional guide surfaces on the template to guide a stylus, which in turn guides a mill guide, which guides the mill.

Two other embodiments of the milling instrument assembly use two-dimensional guide surfaces on the template to guide the stylus, which in turn also guides a mill guide, which guides the mill. These two additional mill instrument assembly embodiments allow the mill to pivot about a point at one end and follow a defined perimeter about the other end to cut the cavity.

The mill cutting path is also guided by the degrees of freedom that the mill guide allows the mill to move with respect to the guide body. In the threeonal dimensional embodiments, the mill guide is rotationally connected to the guide body and acts like a universal joint between the mill and the guide body. In these embodiments, the stylus moves with the mill as the surgeon directs the mill orientation. In the two-dimensional embodiments, the mill guide rotates about the guide body and allows the mill to translate radially along a slot in the mill guide.

BRIEF DESCRIPTION OF THE DRAWINGS

The present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
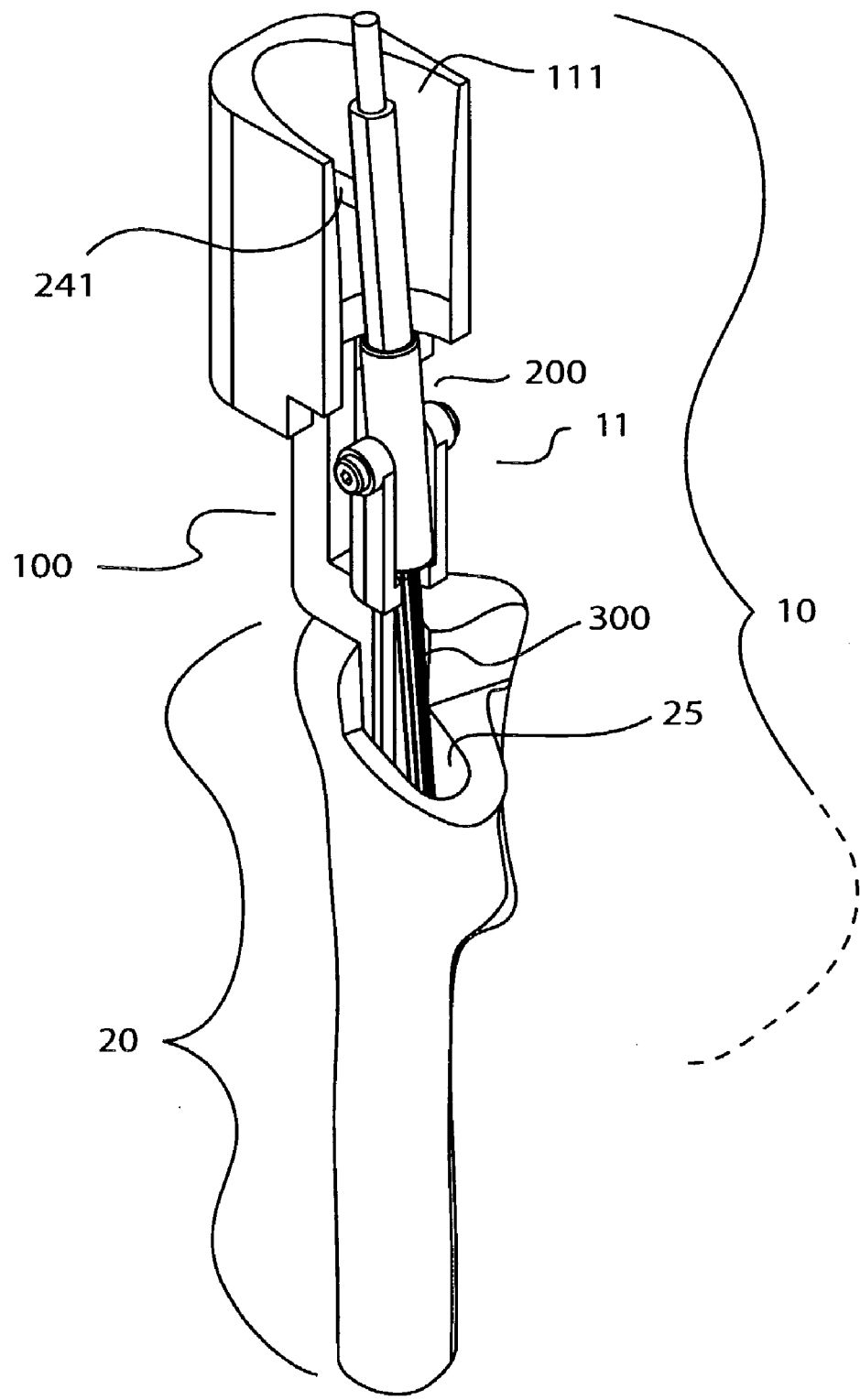
FIG. 1 is a anteromedial perspective view of a first embodiment of a bone milling instrument assembly capable of guiding a mill over a three-dimensional milling surface, shown positioned in a cut proximal femur.

Looking first at FIG. 1, a first embodiment of a milling instrument assembly 10 for shaping a bone cavity 25 in a proximal femur 20 is shown. In FIG. 1, the milling instrument assembly 10 is positioned to prepare the cavity 25 in the proximal femur 20. The milling instrument assembly 10 comprises three major subassemblies that are shown in greater detail in FIG. 2. These subassemblies are: a guide body 100, a mill guide 200, and a tissue cutting mill 300.

Figure 2:
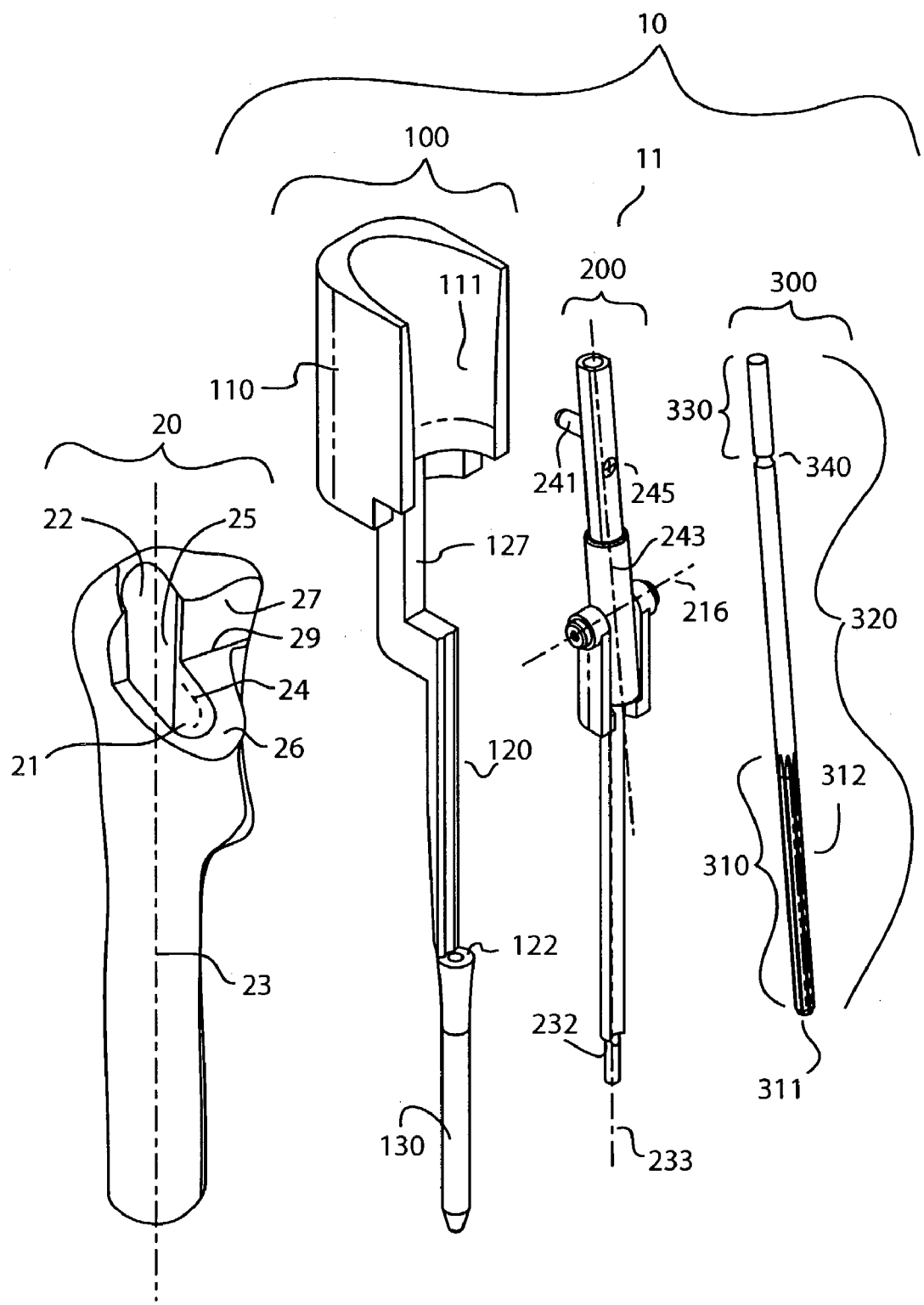
FIG. 2 is an exploded view of FIG. 1, showing the proximal femur, guide body, mill guide, and bone cutting mill.

In FIG. 2, these three subassemblies are shown before assembly and before insertion into the proximal femur 20. As shown in FIG. 2, prior to insertion of the milling instrument assembly 10, some of the tissue is removed from the proximal femur 20 to allow for insertion of the milling instrument assembly 10. During a THA procedure, a surgeon typically removes the diseased femoral head tissue by cutting transverse 26 and longitudinal 27 osteotomy cuts in the bone that intercept along an osteotomy edge 29. The surgeon also drills a bore 22 distally into the medullary canal of the proximal femur 20 along the direction of a femoral anatomic longitudinal axis 23. This bore 22 and these transverse 26 and longitudinal 27 osteotomy cuts are representative of possible cuts made by the surgeon to prepare the proximal femur for milling of the bone cavity 25. Depending on the anatomic structure of the particular patient's diseased hip joint, other preparations, as understood by one familiar with the orthopedic surgical art of THA, may be necessary.

The guide body 100 is temporarily anchored in the bore 22 in the proximal femur 20 during the milling of the bone cavity 25. The other subassemblies of the milling instrument assembly 10, i.e., the mill guide 200 and the mill 300, move with respect to the guide body 100 that is temporarily fixed to the proximal femur 20. Therefore the guide body 100 anchors both the milling instrument assembly 10 in the proximal femur 20 and aids in guiding the mill guide 200 to direct the tissue cutting mill 300 along the preferred cutting path 24 (FIG. 2) of a cutting surface 21 in the bone cavity 25.

Figure 3:
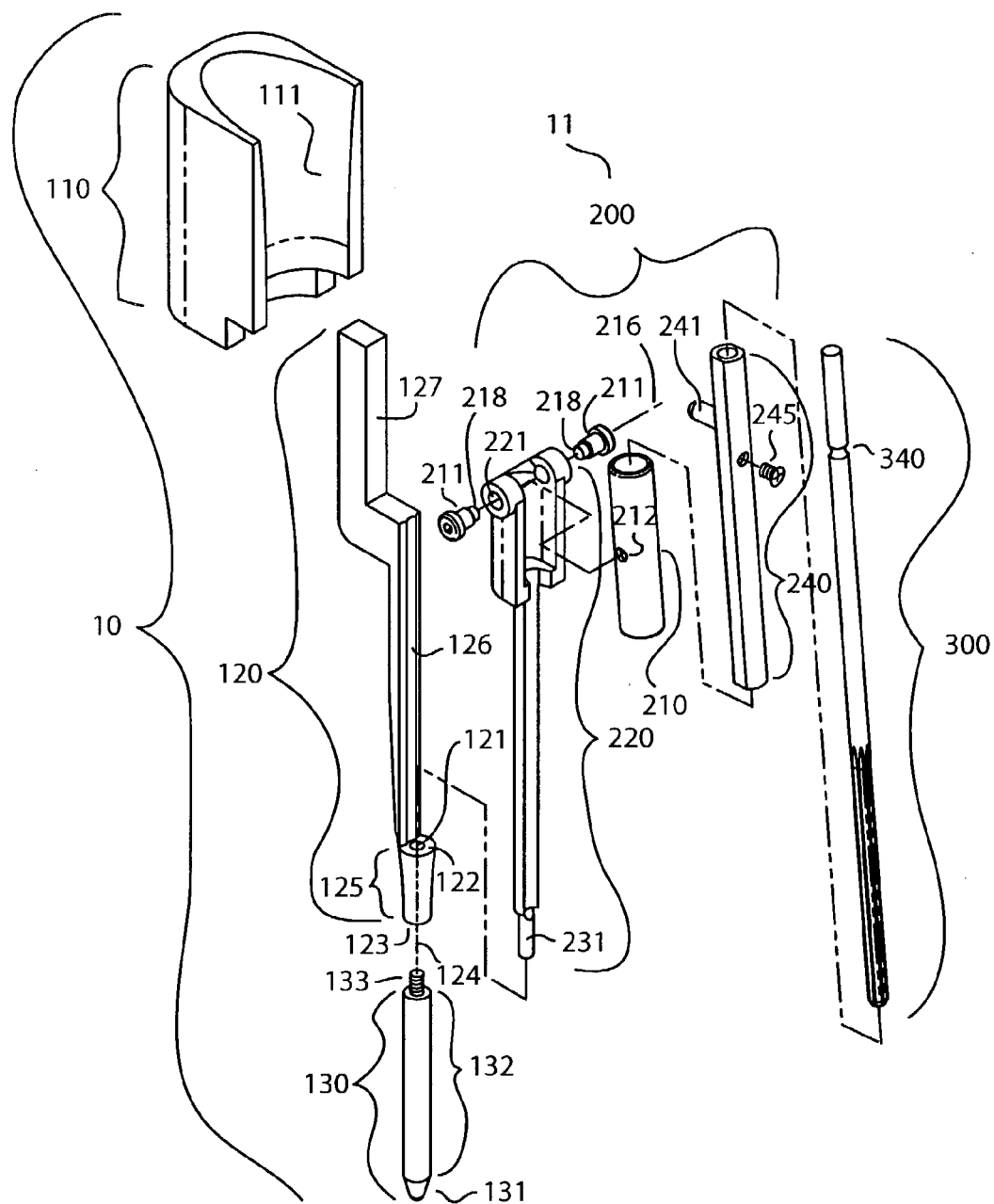
FIG. 3 is an exploded view of individual components of the first embodiment of the bone milling instrument assembly of FIG. 1.

As shown in FIGS. 2, 3 and 4, the guide body 100 preferably comprises a guide body frame 120, a distal stem 130 and a template section 110. The distal stem 130 is made available to the surgeon in a range of diameters and lengths to best fit the dimensions of the pre-drilled bore 22 in the proximal femur 20. The distal stem 130 essentially helps to hold the guide body 100 in place during the milling of the bone cavity 25. As shown in FIG. 3, distal stem 130 has a distal section 131 dimensioned to fit into the femoral bore 22 and a proximal section 132 provided with a connection element 133. This connection element 133 is shown as a threaded element in FIG. 3. However, the connection element 133 can comprise any sturdy, removable connection element such as a press fit, a spring lock, a bayonet lock, a tongue and groove element or similar connection element. The connection element 133 is dimensioned to mate with a mating connection element 123 (FIG. 3) on a distal section 125 of the guide body frame 120.

The diameter of the distal section 125 of the guide body frame 120 is typically similar in size to that of the smallest diameter distal stem 130. This allows the guide body frame 120 to mount any size distal stem 130 without the guide body frame's distal section 125 unduly interfering with the walls of the bone bore 22.

Hence, the surgeon selects one distal stem 130 from a plurality of distal stems 130 that best fits inside the femoral bore 22. This provides a sturdy base for the remainder of the milling instrumentation throughout the cavity milling procedure. The surgeon then connects the selected distal stem 130 to the distal end of guide body frame 120, mounts the remaining components to the guide body frame, and then inserts the guide body frame into the bore 22 in the proximal femur 20.

As shown in FIG. 3, the guide body frame 120 is divided into three sections; the distal section 125, a middle section 126 and a proximal guide body frame section 127.

Along with being dimensioned to accept the distal stem 130, the guide body frame 120 is also dimensioned to allow constrained movement of the mill guide 200 relative to guide body frame 120 (and hence relative to the proximal femur 20), and to allow releasable connection of the template section 110.

The mill guide 200 turns along a longitudinal axis 124 of a receptacle 121 (FIG. 3) in a bearing surface 122 of the distal section 125. These features are shown in FIG. 3. This allows one of the degrees of freedom associated with the function of the mill guide 200; the rotation around a mill guide axis 233 shown in FIG. 2. The kinematic relationship between the guide body 100, mill guide 200 and tissue cutting mill 300 will be discussed more thoroughly after a detailed discussion of the mill guide 200.

Referring again to FIG. 3, the template section 110 can be releasably secured to the proximal guide body frame section 127. Since the template section 110 can be removably connected to the guide body frame 120, a plurality of template sections 110, each with a unique guide surface 111 contour, can be supplied to the surgeon. This allows the surgeon the opportunity to select the best template section 110 at the time of surgery and connect it to the guide body frame 120. This template section 110, in combination with the mill guide 200, will guide the tissue cutting mill 300 along a preferred cutting path 24 (FIG. 2) indicated for the procedure.

Figure 4A:
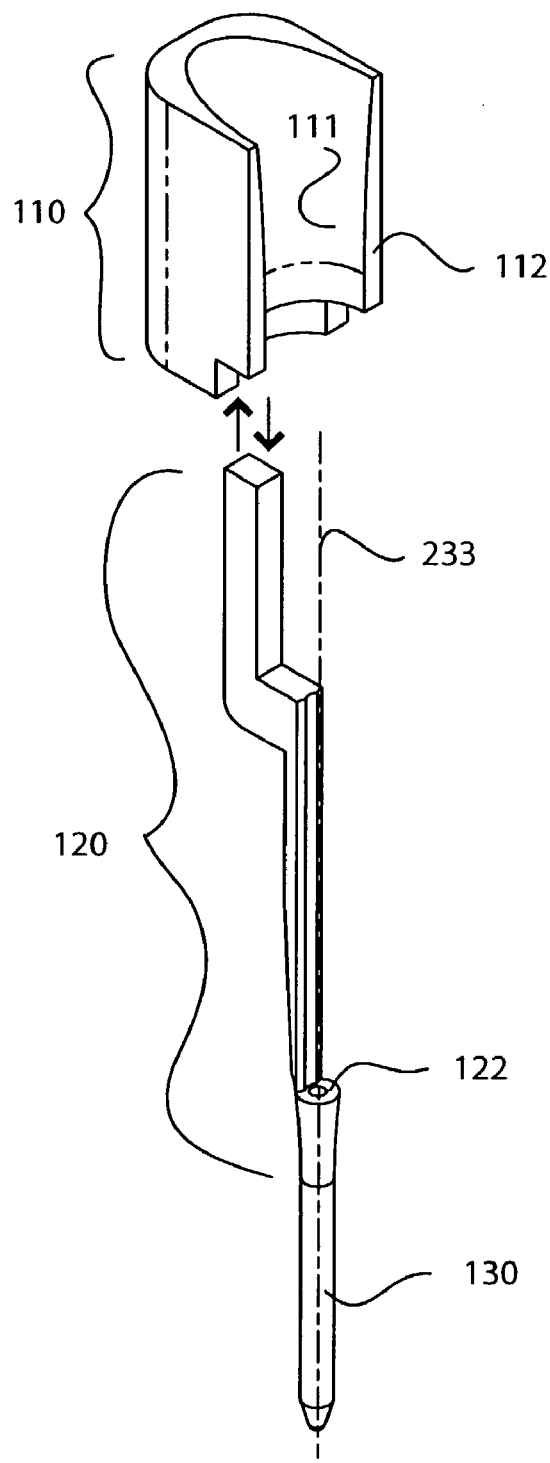
FIG. 4A is a perspective view of a first embodiment of the guide body subassembly of the bone milling instrument assembly of FIG. 1, showing the guide body frame and a releasably securable template section.

In the embodiments shown in FIG. 2, 3 and FIG. 4A, the connection between the template section 110 and the proximal guide body frame section 127 is a tongue and groove type connection. However, other types of connections in which the template section 110 is removably connectable to the proximal section 127 can be used. These removably connectable connections include those commonly used in mechanical fastening, such as tapered, threaded, spring lock, cam lock, and press fit, pinned, collet, adjustable screw lock, adjustable threaded, rack and pinion, and meshing gear mechanism.

Figure 4B:
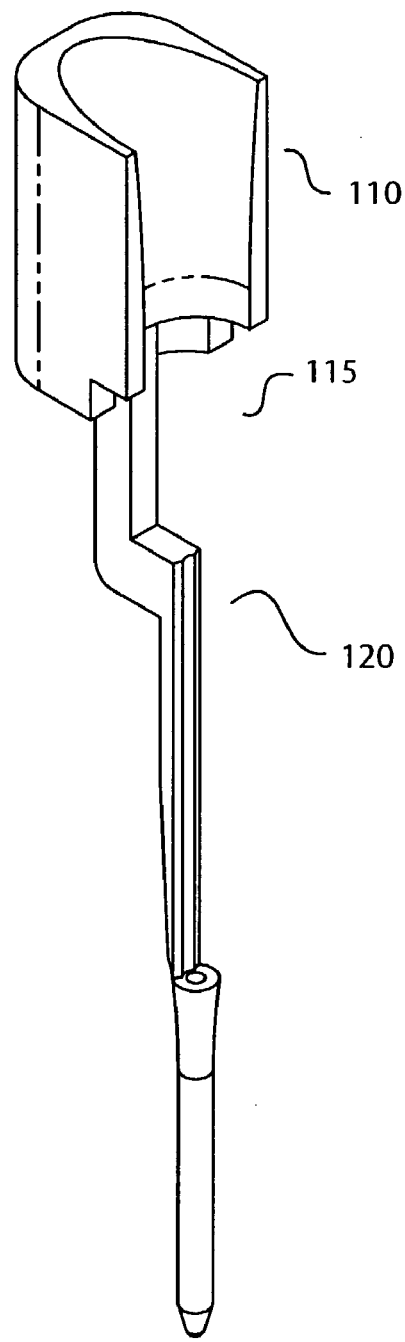
FIG. 4B is a perspective view of a second embodiment of the guide body subassembly of the bone milling instrument assembly of FIG. 1, showing the template section rigidly secured to the guide body frame.

Alternatively, the template section 110 could be permanently connected to the guide body frame 120, such as shown in FIG. 4B, so as to form a guide body structure 115.

This alternative embodiment requires a plurality of guide body structures 115 that are appropriately shaped to cover the range of cavity sizes and shapes needed for a modular implant system.

Figure 5:
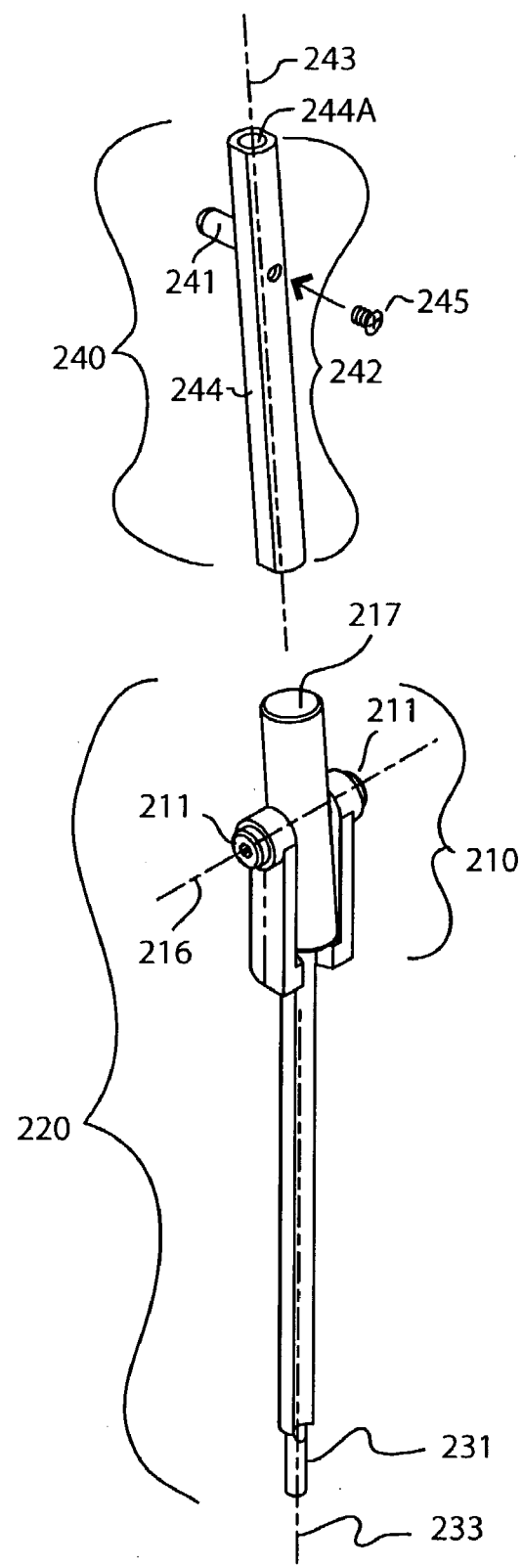
FIG. 5 is a perspective view of the mill guide subassembly associated with the bone milling instrument of FIG. 1, showing a follower slidably removed from a pivot guide.
Figure 6:
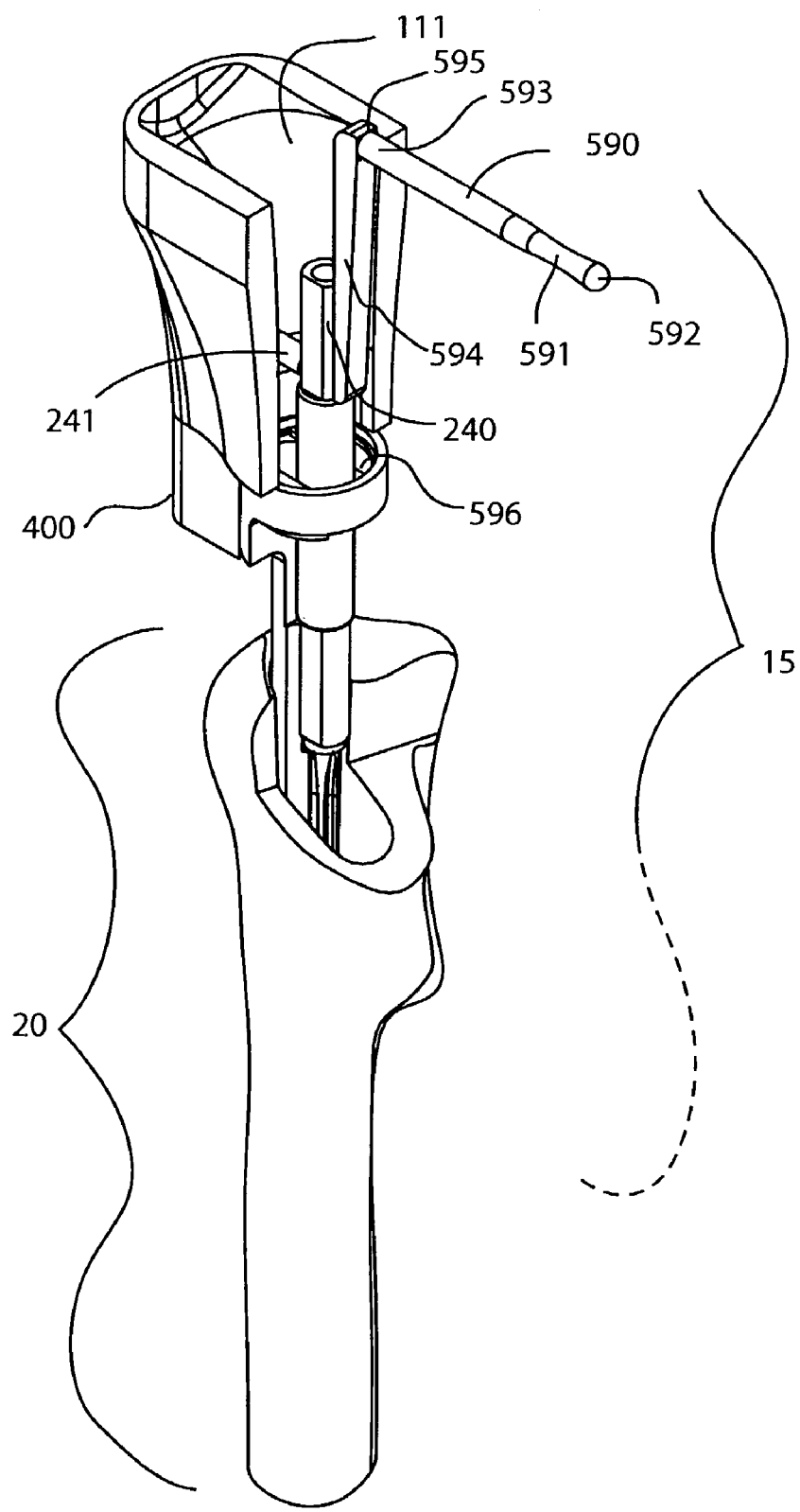
FIG. 6 is a perspective view of a second embodiment of a bone milling instrument assembly in a proximal femur, showing an embodiment of the guide body with a rotary bearing connection to the mill guide.
Figure 7:
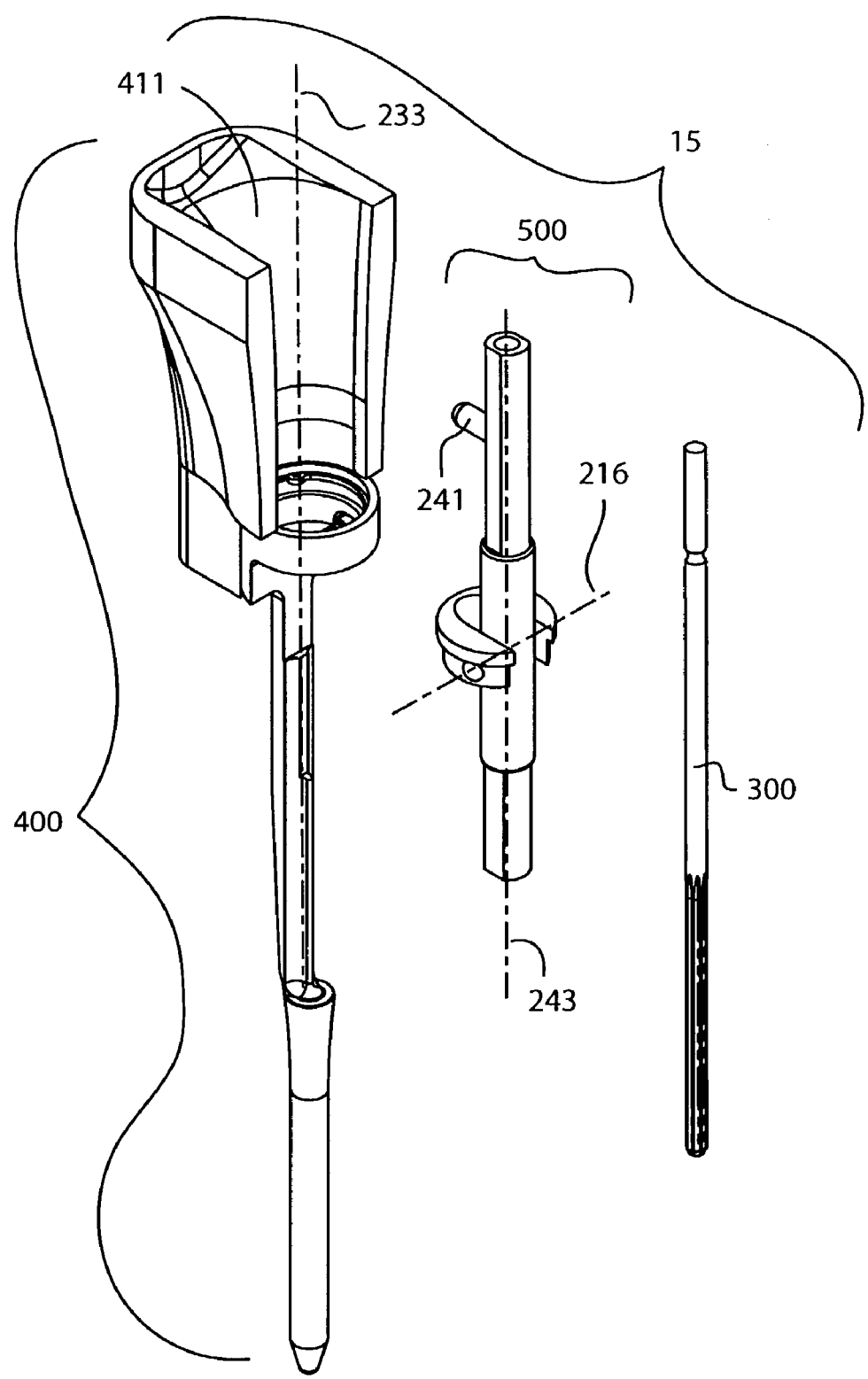
FIG. 7 is a partially exploded view of the bone milling instrument of FIG. 6, showing the guide body, the mill guide, and the mill.
Figure 8:
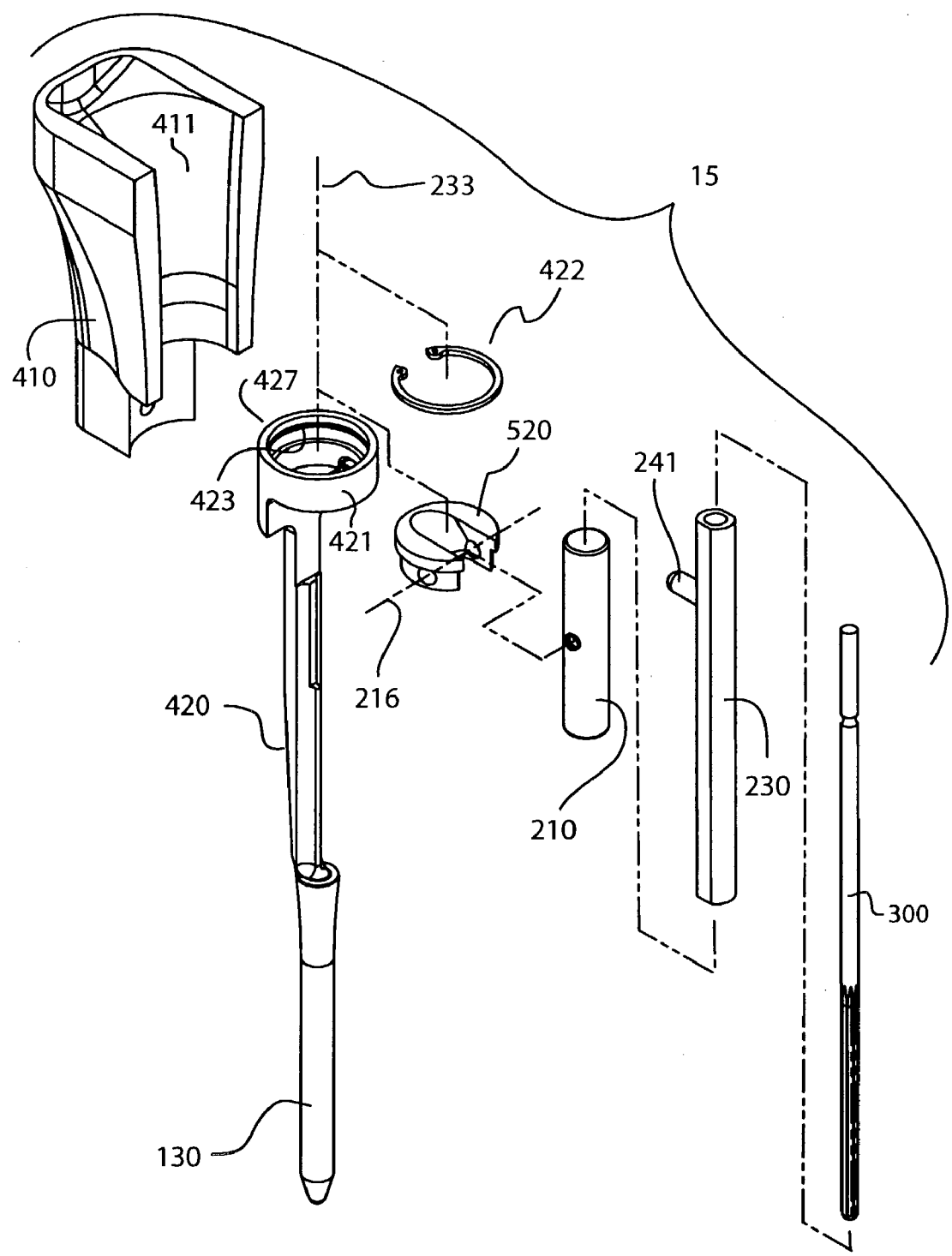
FIG. 8 is a fully exploded view of the bone milling instrument of FIG. 6.

The second major subassembly of the milling instrument is the mill guide 200. A first embodiment 11 of the mill guide 200 is shown in FIGS. 1, 2, 3 and 5. A second embodiment 15 of the mill guide 200 is shown in FIGS. 6, 7, and 8. A third embodiment 12 of the mill guide is shown in FIGS. 9, 10, 11, 12, 13, and 14. The first embodiment 11, second embodiment 15 and third embodiment 12 of the mills guide will each be discussed in detail. Either first embodiment 11, second embodiment or third embodiment of the mills guide 200 works in conjunction with the template section 110 to orient the mill 300 in the direction of the tissue to be removed from the bone cavity 25. The mill guides 200 essentially work as a universal joint between the mill 300 and the guide body 100. When a non-axial force is applied to the mill 300, this force is constrained by the mill guide 200 to an orientation that is both pivoting along a pivot guide axis 216 (FIG. 3) and rotating along the mill guide axis 233 (FIG. 5).

Looking next at the first embodiment of the mill guide 200 in FIG. 5, there are shown the main components of one embodiment of a mill guide 200 that is designed to cooperate with the components shown in FIGS. 1, 2, 3, 4A and 4B. These components are a pivot guide 210, an arbor 220, and a follower 240.

The first embodiment of the mill guide 200 allows the pivot guide 210 to pivot around the pivot guide axis 216. The pivot guide 210 has a rotation-constraining feature in a bore 217 that allows the follower 240 to slide longitudinally in the direction of a mill sleeve axis 243 but not rotate substantially about that axis 243. In the first embodiment shown in FIGS. 1, 2, 3, 4, and 5 the aforementioned rotational constraint is done by inner ends 218 (FIG. 3) of the pivot pins 211 that mate with flat surfaces 244 on the follower 240. As the follower 240 slides within the pivot guide 210, the inner ends 218 of the pivot pins 211 prevent the follower 240 from rotating about the mill sleeve axis 243.

The pivot guide 210 also allows pivoting with respect to the arbor boss 220 around the pivot guide axis 216. In the first embodiment 11 of the mill guide 200 shown in FIGS. 1, 2, 3, 4, and 5, this rotation is constrained to the pivot guide axis 216 by the pivot pins 211 that are free to rotate around the pivot guide axis 216 inside the arbor boss 221. The pivot pins 211 are connected to pivot pin receptors 212 on the pivot guide 210. Once assembled, the pivot guide 210 rotates in the arbor boss 221 of the arbor 220 (FIG. 3), around the pivot guide axis 216. This permits the mill 300 to rotate through one of the two degrees of axial freedom allowed by the mill guide 200.

The first embodiment 11 of the mill guide 200 shown in FIGS. 1, 2, 3, and 5 utilizes pinned connections with respect to rotational movement between the pivot guide 210 and the arbor boss 220. However, other types of connections, including pinless radial tongue and radial groove joints and pin-groove joints, could be used as the connection mechanism to allow the same rotation.

The second degree of rotational freedom is that the mill guide 200 rotates around is the mill guide axis 233 (FIG. 2). In the first embodiment shown in FIGS. 1, 2, 3, 4, and 5, the mill guide assembly 200 is constrained to rotate around the mill guide axis 233 by a rotary joint shaft 231 (FIG. 5) and a guide body frame receptacle 121 (FIG. 3). In this first embodiment, the mill guide 200 is also constrained from translating distally down the longitudinal axis 23 of the proximal femur 20 by the interference between a rotary joint bearing surface 232 and the guide body frame bearing surface 122. However, the mill guide 200 can be removed from the guide body 100 by pulling the rotary joint shaft 231 out of the guide body frame receptacle 121 in the guide body 100.

The mill 300 has a distal tissue cutting section 310 to remove tissue, a shaft 320 running longitudinally the length of the mill 300, and a proximal section 330 that can be connected to a power tool (not shown) or a hand tool (also not shown) that drives the mill 100 through a motion that results in the mill tissue cutting section 310 removing tissue from the cavity 25 in the proximal femur 20.

The mill 300 is intended to represent any tissue removal instrument suitable for use in the surgical environment that can mill, cut, drill, or plane tissue. The mill 300 has a longitudinal shaft 320 that is dimensioned to slide, and when needed rotate, within a longitudinal bore 244A (FIG. 5) in a mill sleeve 242. In this embodiment the mill sleeve 242 is in the follower 240 that is a component of the mill guide subassembly 200. However, in other embodiments, the dimensional constraints of the transverse cross-section of the mill shaft 320 may be different than those for this embodiment.

The mill 300 shown in the embodiment of FIGS. 1, 2, and 3 is generally circular in cross-section. Although the shape of this mill 300 embodiment implies the conversion of rotary motion to cutting, one of ordinary skill in the art will appreciate that the mill 300 can be dimensioned to other suitable constructs that allow bone material to be removed from the cavity. Any form of energy including rotary, oscillatory, or vibratory motion can drive the mill 300. The geometry and shape of the distal cutting tip 311 and the cutting flutes 312 on the tissue cutting section 310 are designed to optimize the cutting ability of the mill 300 based on the type of movement and energy that drive the mill 300.

The distal cutting section 310 of the mill 300 contains a distal cutting tip 311 that allows the mill 300 to remove tissue from the cavity 25 in-line with the axis of the shaft 320. The mill 300 also contains cutting flutes 312 that allow the mill 300 to cut material along the side of the shaft 320 as the mill is moved through the cavity 25.

The proximal section 330 of the mill 300 is dimensioned to be releasably connected to a mechanism like a drill chuck (not shown) or mill collet (not shown) or other connecting device (not shown) on a power tool (not shown) or hand tool (not shown) such that the motion and energy of the tool is translated to the mill 300 during operation.

The mill 300 also has a translation semi-resisting lock feature 340 shown as a circumferential groove in the shaft 340 of the mill 300 in FIG. 3. This lock feature 340 allows the mill 300 to semi-translationally lock along the mill sleeve axis 243 into the corresponding lock mating feature 245 in the follower 240 of the mill guide subassembly 200 such that the mill distal section 310 can still cut tissue. As the distal section 310 cuts tissue, the mill 300 is capable of carrying the follower 240 in the same general longitudinal direction along the longitudinal mill sleeve axis 243 as the mill 300 is directed by the operator. This lock feature 340 has enough clearance between it and the corresponding lock mating feature 245 to allow the mill 300 to rotate and translate as needed to cut tissue from the bone cavity 25.

The template section 110 and the guide body 100 further constrain the tissue cutting section 310 of the mill 300 to follow the preferred cutting path 24 that is oriented along a preferred cavity surface 21.

Each template section body 112 has a guide surface 111 that is uniquely dimensioned proportionally to that of the desired cavity surface 21 shape. Hence, as a stylus 241 of the mill guide 200 follows the contour of the guide surface 111, the tissue cutting section 310 of the mill 300 is oriented in a direction to remove the tissue, thereby creating the cavity surface 21 of the cavity 25.

A second embodiment 15 of the milling instrument assembly 10 is shown in FIGS. 6, 7, and 8. This second embodiment of the milling instrument assembly 15 comprises a guide body with circular bearings 400 (FIG. 6). As shown in FIG. 7, this instrument embodiment 15 is also made of three subassemblies that function similarly to those of the first embodiment of the milling instrument assembly 10 shown in FIG. 1. These subassemblies are the second embodiment of the second embodiment of a guide body 400, a circular mill guide 500, and the mill 300.

The second embodiment of the guide body 400 of the second embodiment 15 of the milling instrument assembly 10 has a circular bearing 421 that receives a retaining ring 422 in an internal circular groove 423 that prevents the circular arbor 520 of the circular mill guide 500 from translating axially. However, the circular mill guide 500 is free to rotate around the mill guide axis 243 (FIGS. 5 and 7) in much the same way that the mill guide 200 is free to rotate about that same mill guide axis 233. Although a retaining ring 422 is shown in this embodiment, other embodiments known to one skilled in the art of rotational connections such as radial pins and threaded retaining rings can also provide the same function as the retaining ring 422 to keep the circular mill guide 500 axially constrained in the circular bearing 421 to allow rotation around the mill axis 433.

A template section 410 can be releasably secured to the proximal guide body frame 427. Since the template section 410 can be removably connected to guide body frame 420, a plurality of template sections 410, each with a unique guide surface 411, can be supplied to the surgeon. This template section 410, in combination with the mill guide 500, will guide the mill 300 along the preferred cutting path 24 (FIG. 2) indicated for the procedure.

The second embodiment of the milling instrument assembly 15 of FIGS. 6, 7, 8 works in conjunction with the circular mill guide 500 shown in FIG. 7. The mill guide 500 essentially works as a universal joint between mill 300 and guide body 100. When a non-axial force is applied to the mill 300, this force is constrained by the circular mill guide 500 to an orientation that is both pivoting along the pivot guide axis 216 and rotating along the mill guide axis 243.

A handle 590 is shown in FIG. 6 that can be rigidly attached to the follower 240 of either of the above described mill guide 200 or the circular mill guide 500. This handle 590 is generally comprised of a guidance section 293 that facilitates the gripping and guidance by the hand of a surgeon (not shown) and a connection portion 594 that mounts to the follower 240. The guidance section 293 has a grip portion 591 positioned along the longitudinal shaft of the guidance section 293. This grip portion 591 is used for gripping or making contact with the user (not shown). The guidance section also has a guidance section connection 595 on the end opposite the grip portion 591 to connect to the connection portion 592. The connection portion 592 connects to the follower 240 in any method that does not interfere with the movement of the mill guide instrument assembly 10 or the second embodiment of the mill guide instrument assembly 15. These methods of attachment can be permanent such as fused, integral or welded connections or can be non-permanent, removable connections such as threaded, slotted, or pinned connections. During the milling process, the surgeon uses the handle 590 to help directly guide the stylus 241 with one hand while driving the mill 300 with other hand. However, more than one person can perform these concurrent tasks.

In the second embodiment of the milling instrument assembly 15 of FIGS. 6, 7, and 8, the mill guide 500 and the second embodiment of the guide body 400 are constrained by a circular bearing joint 596 that provides similar movement of the second embodiment of the milling instrument assembly 15 around the mill guide axis 233 as discussed above for the first embodiment of the milling instrument assembly 10.

Figures 9, 10:
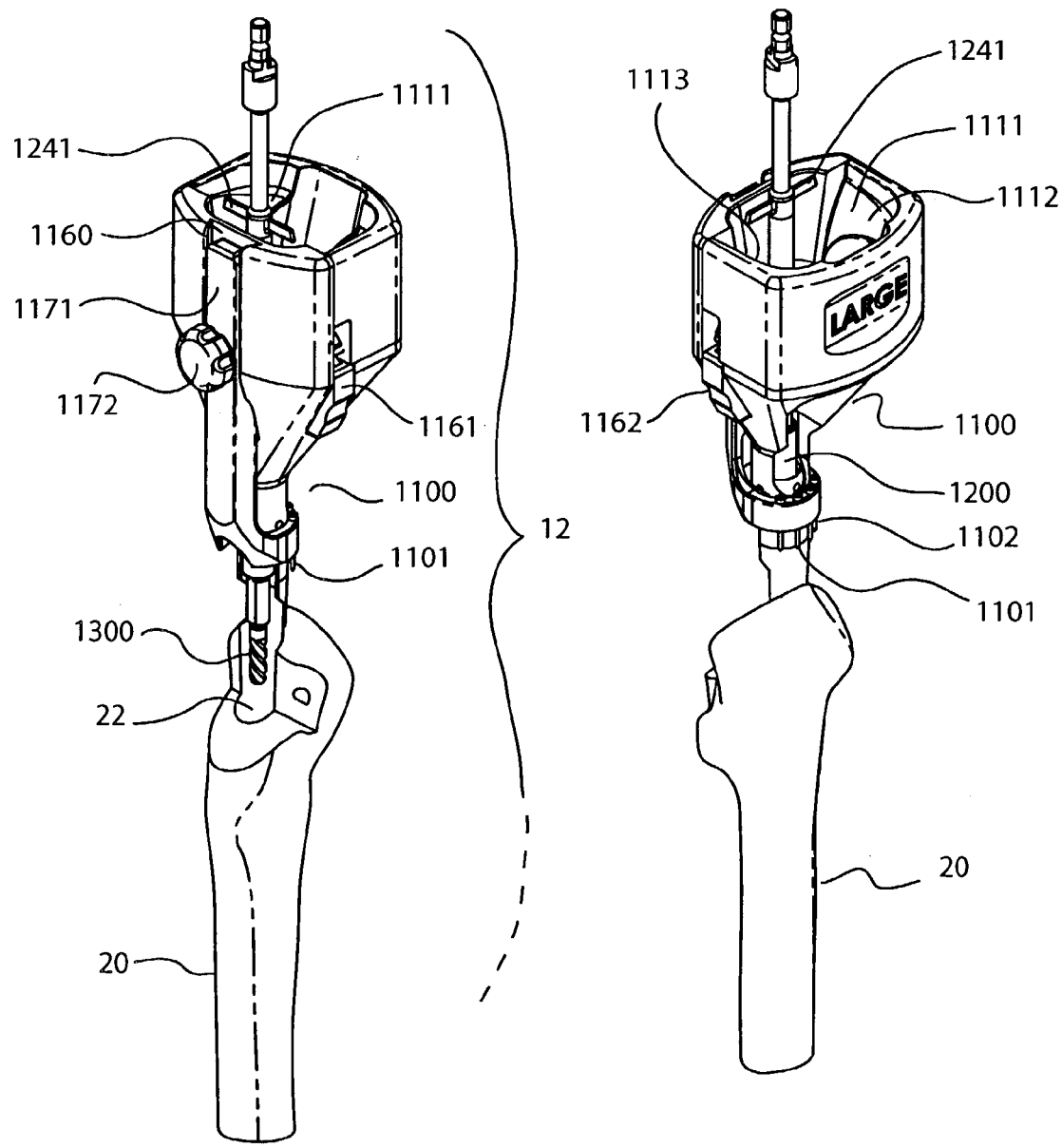
FIG. 9 is an anteromedial perspective view of a third embodiment of a bone milling instrument assembly capable of guiding a mill over a three-dimensional milling surface, shown during positioning and prior to securing to a cut proximal femur.
FIG. 10 is a posterolateral perspective view of the bone milling instrument assembly shown in FIG. 9.
Figure 11:
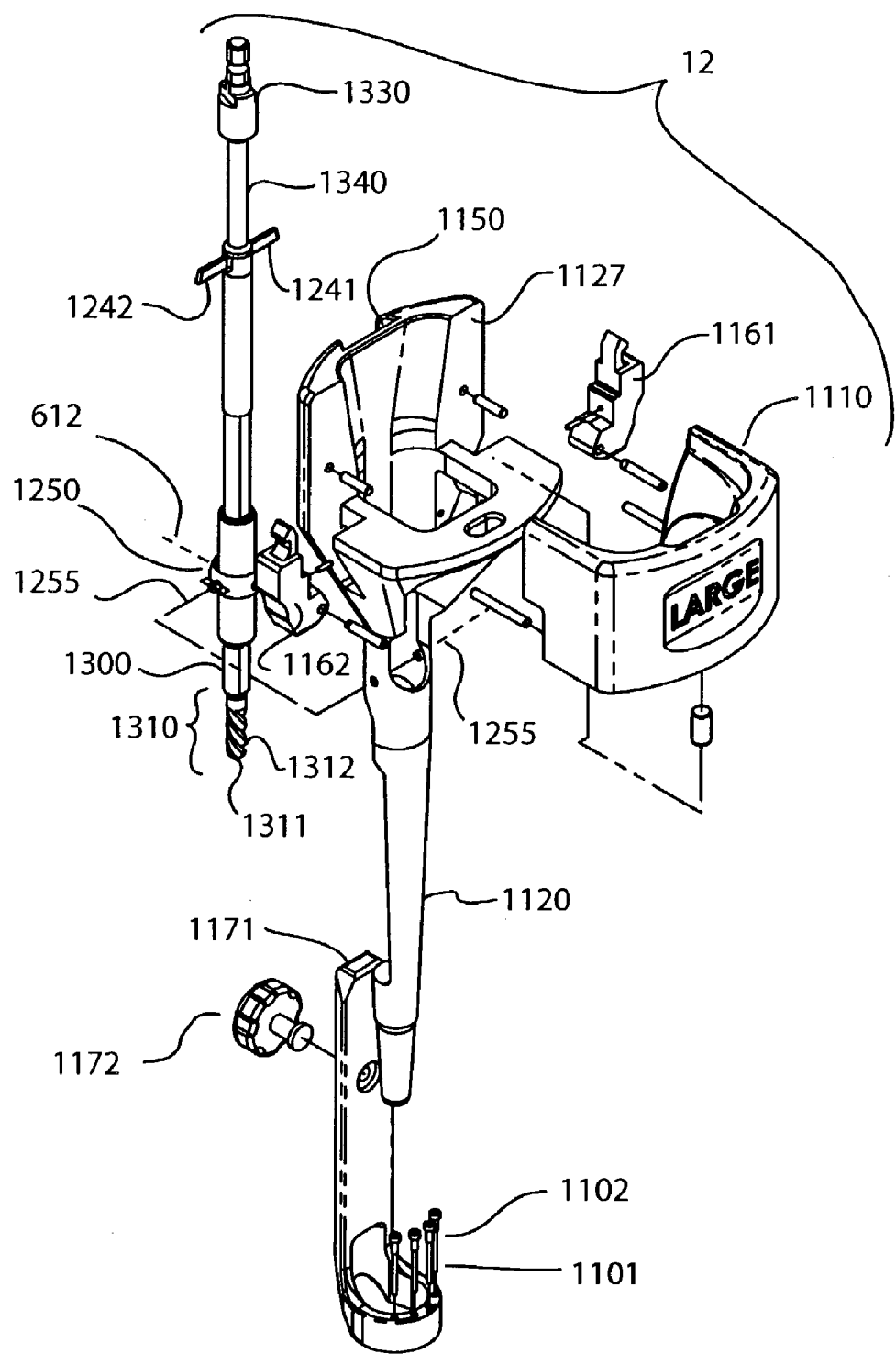
FIG. 11 is an exploded view of the bone milling instrument assembly shown in FIG. 9.
Figure 12:
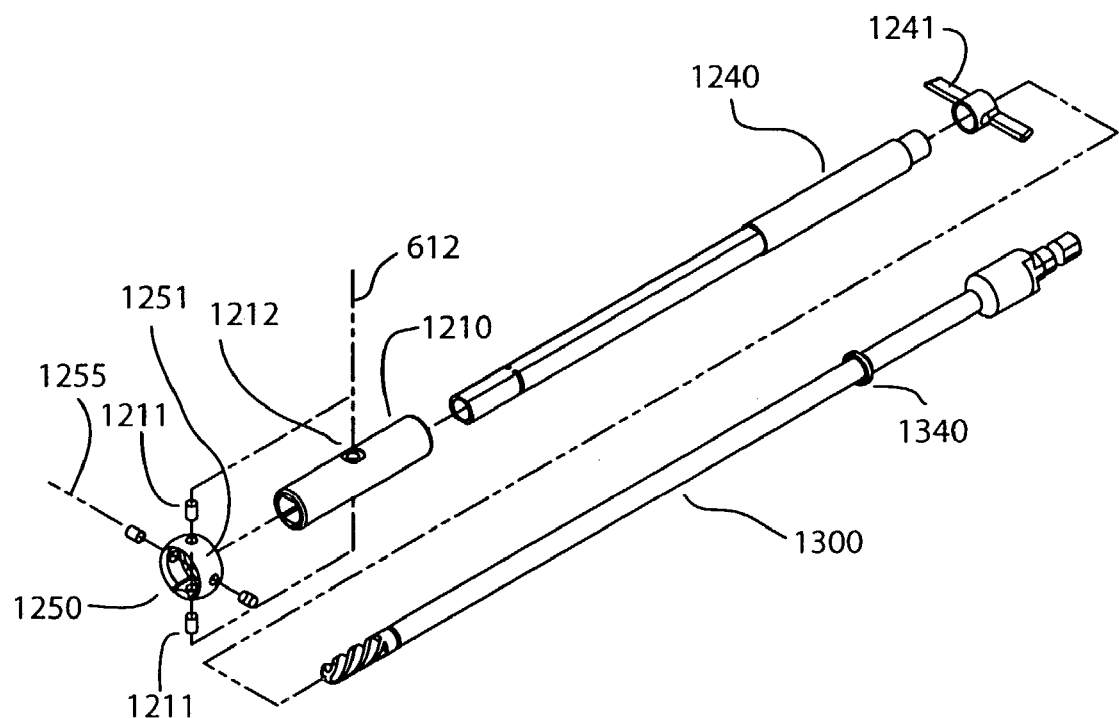
FIG. 12 is an exploded view of the subassembly of the mill guide and the mill of the bone milling instrument assembly shown in FIG. 9.

A third embodiment 12 of the milling instrument assembly 10 is shown in FIGS. 9, 10, and 11. This third embodiment of the milling instrument assembly 12 comprises a third embodiment of the guide body 100, and a third embodiment of a mill guide 1200. As shown in an anteriomedial view in FIG. 7, this third embodiment of the milling instrument assembly 12 enters the bore 22 in the proximal femur 20 and is rotationally positioned to create a bone cavity in the orientation to match the modular implant orientation. The guide body is secured to the proximal femur by a securing means 1101. In FIG. 9 and FIG. 10, the securing means 1101 is a plurality of pins 1102 that connect the third embodiment of the milling instrument assembly 12 to the proximal femur 20. However, other securing means such as screws, clamps, clips, and gripping teeth can also be used to connect the instrument assembly 12 to the proximal femur 20. Although not shown in previous figures of the first embodiment of the milling instrument assembly 10 or second embodiment of the milling instrument assembly 15, the securing means 1101 can be adapted to secure the mounting of these and any embodiment of the milling instrument assembly to the bone.

The third embodiment of the guide body 1100 has a universal joint connection 1250 between it and the third embodiment of the mill guide 1200. This universal joint connection 1250 allows the third embodiment of the mill guide 1200 and the universal joint housing 1251 to pivot along the pivot guide axis 216 and allows the universal joint housing 1251 and the third embodiment of the guide body 1100 to pivot along the universal joint axis 1255. This combination of two rotational degrees of freedom allows the third embodiment of the mill guide 1200 the rotation necessary to guide the tissue cutting section 310 of the mill 300 or the tissue cutting section 1310 of the second embodiment of the mill 1300 rotationally towards any position within the boundaries of the geometry of the desired cavity. The mill 300 and the second embodiment of the mill 1300 slide within the pivot guide 1210 of the guide body 1200. This allows the mill 300 or 1300 to translate to the towards any position within the geometry of the desired cavity. The combination of translation and two rotational degrees of freedom allow the mill 300 or the second embodiment of the mill to reach any position desired.

Although a Hookes type universal joint with degrees of freedom about two approximately perpendicular axis is shown in FIGS. 9, 10, 11, 12, 13, and 14, other types of universal joints such as Bendix-Weiss rolling ball, Rzeppa, Traca, and double Cardan type universal joins can be adapted to provide conical rotational degrees of freedom between the third embodiment of the guide body 1100 and the third embodiment of the mill guide 1200.

A template section 1110 shaped to guide the second embodiment of the mill guide 1200 to the desired cavity shape is releasably secured to the second embodiment of the guide body frame 1120. Since the template section 1110 can be removably connected to the proximal guide body frame 1127, a plurality of template sections 1110, each with a unique guide surface 1111, can be supplied to the surgeon. This template section 1110, in combination with the third embodiment of the mill guide 1200, will guide the second embodiment of the mill 1300 along the preferred cutting path 24 (FIG. 2) indicated for the procedure.

In the third embodiment of the milling instrument assembly 12 shown in FIGS. 9, and 10 the connection between the template section 1110 and the proximal section 1127 of the guide body frame 120 is a tongue and groove type connection. The tongue 1171 on the second embodiment of the body frame 1120 is dimensioned to axially translate along the groove 1160 in the template section 1110. The locking screw 1172 provides a frictional wedge fit between the tongue 1171 and the groove 1160 at he desired location that aligns with the desired axial position of the proposed cavity.

Figure 13:
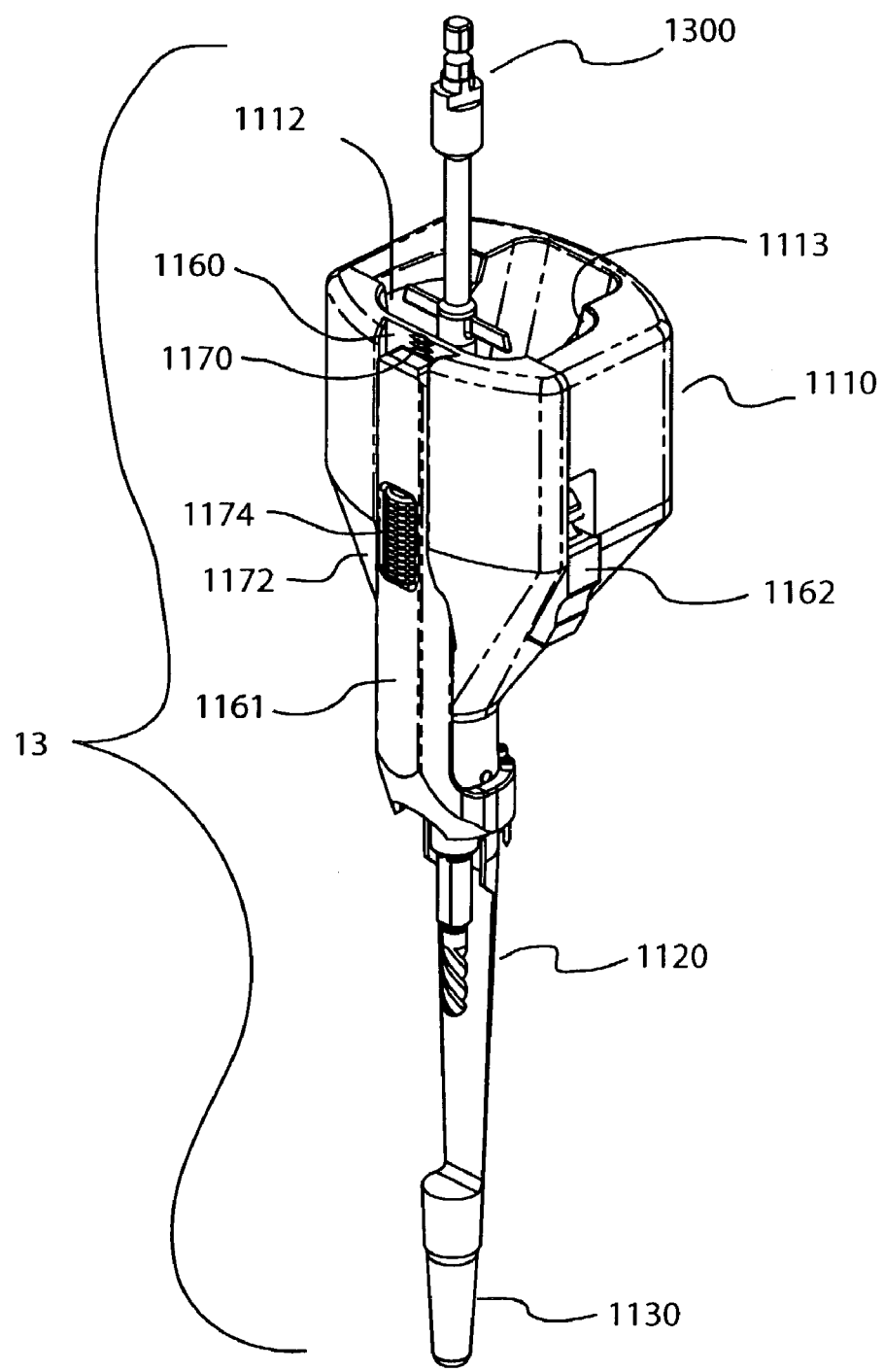
FIG. 13 is an anteriomedial view of a fourth embodiment of a bone milling instrument assembly in which the template is adjusted by a threaded adjustable thumb screw.
Figure 14:
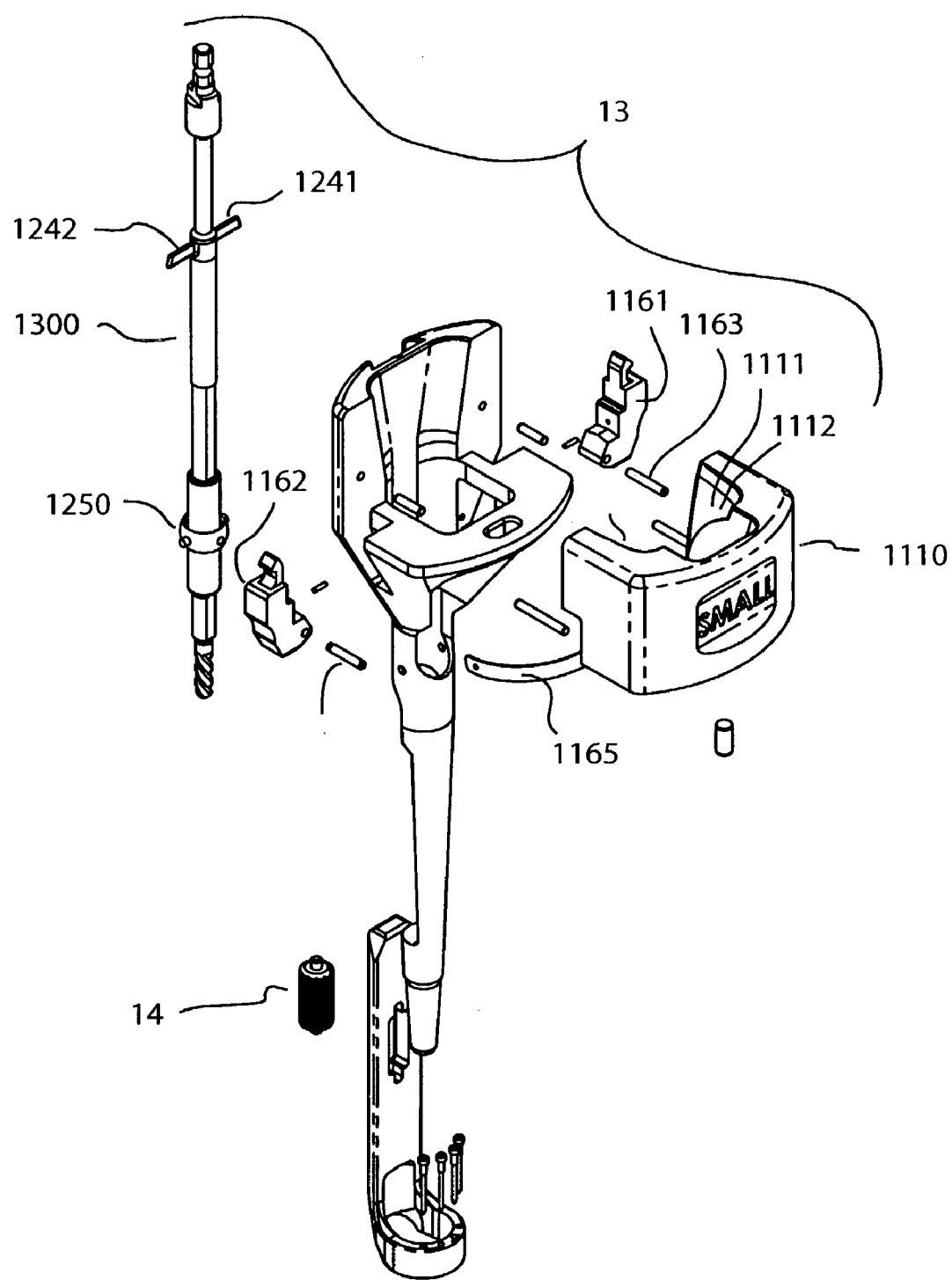
FIG. 14 is a exploded view of the bone milling instrument assembly shown in FIG. 13.

In the fourth embodiment of the milling instrument assembly 13 shown in FIG. 13 and FIG. 14, the template section 1110 is axially adjustable with respect to the tongue 1171 and groove 1160 sliding axis by a thumb screw 1170. The thumb screw 1170 is allowed to rotate along its axis, but is axially captured in translation in the tongue 1171. The male helical threads 1174 on this thumb screw 1170 mate with truncated female helical threads 1170 in the groove 1160. The template section 1110 is thus adjusted axially by rotating the thumb screw 1174.

Other types of adjustable connections in which the longitudinal position of the template section 1110 is adjusted with respect to the guide body frame 1120 can be used. These adjustable connections include those commonly used in mechanical fastening, such as cam locks, rack and pinion connections and meshing gear mechanism connections.

In both the third embodiment of the milling instrument assembly 13 and the forth embodiment of the milling instrument assembly 13, the guide surface 1111 contour of the template section 1110 is divided into a first noncontiguous section 1112 and a second noncontiguous section 1113. The separation of these guide surface 1111 into two noncontiguous sections permits better surgeon visualization of the milling site and a greater extent of movement of the mill guide 1200. This greater extent of movement allows for greater accuracy. The first stylus 1241 contacts the guide surface 1111 of the first noncontiguous section 1112, the second stylus 1242 contacts the guide surface 1111 of the second noncontiguous section 1113. As the mill guide 1200 is plunged further distally into the bore 22, the difference between the distance between contact between the first stylus 1241 and the first noncontiguous section 1112, and the distance between the second stylus 1242 and the second noncontiguous section 1113 decreases to the point of convergence such that the first stylus 1241 and the first noncontiguous section 1112 are in contact and simultaneously the second stylus 1242 and the second noncontiguous section 1113 are in contact.

The template section 1111 of the third embodiment of the milling instrument assembly 12 and the fourth embodiment of the milling instrument assembly as removably connected to the guide body proximal section 1127 by a first spring lock 1161 on the anterior and a second spring lock 1162 on the posterior side. The first spring lock is secured to the guide body proximal section 1127 by a first spring lock pin. The second spring lock is secured to the guide body proximal section 1127 by a second spring lock pin. A spring lock band 1165 wraps around the template section 1110 and removably engages with the first spring lock 1161 and the second spring lock 1162 such that the engagement secures the template section 1110 to the guide body proximal section 1127. Other means of removably securing the template section 1110 to the proximal section 1127 such as screws, locking pins, snap rings, and interference fit connections can also be adapted for use for a temporary fixation means between these two elements.

Figure 15:
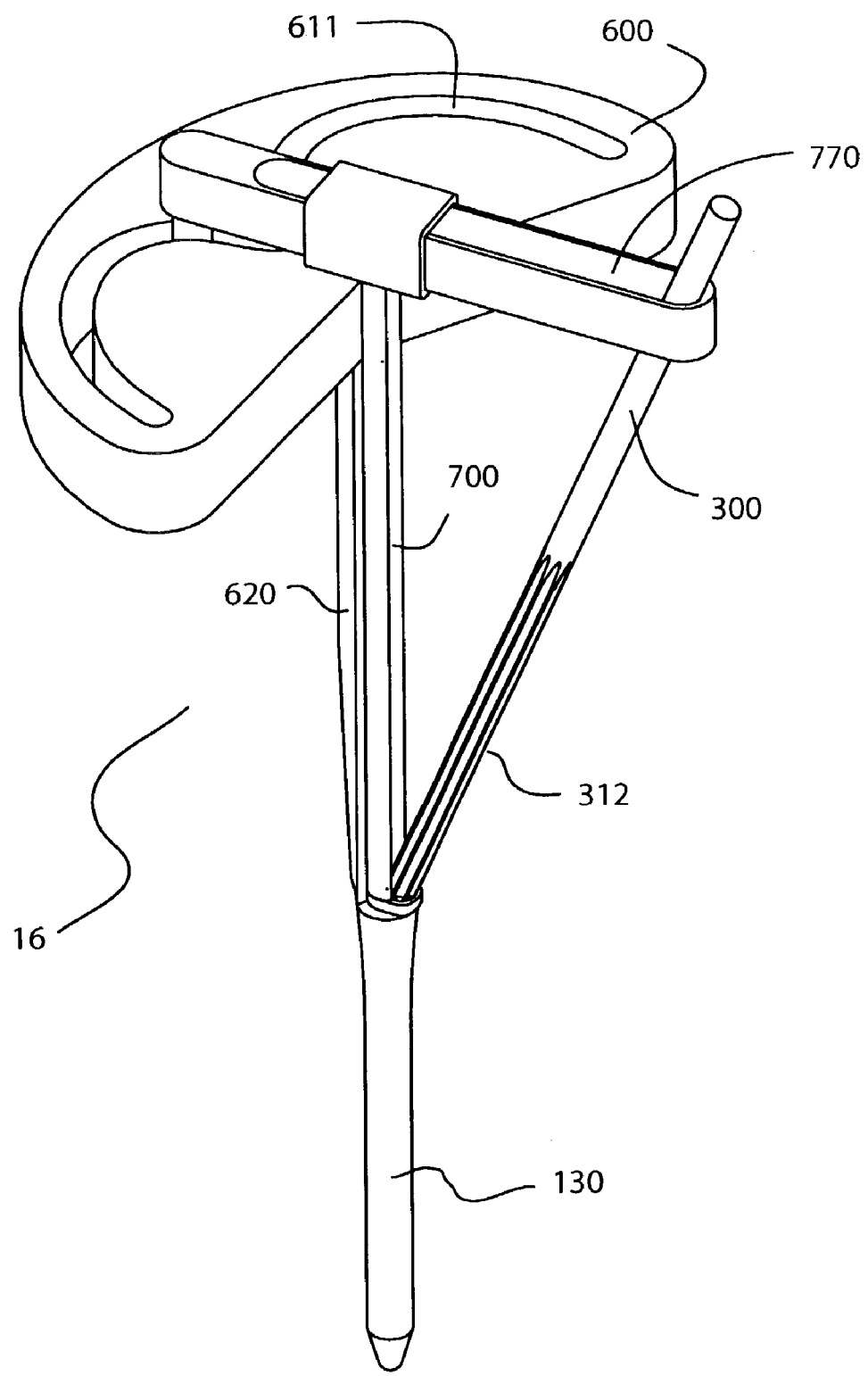
FIG. 15 is a perspective view of a fifth embodiment of a bone milling instrument assembly that uses a two-dimensional template to guide a stylus that guides a mill.
Figure 16:
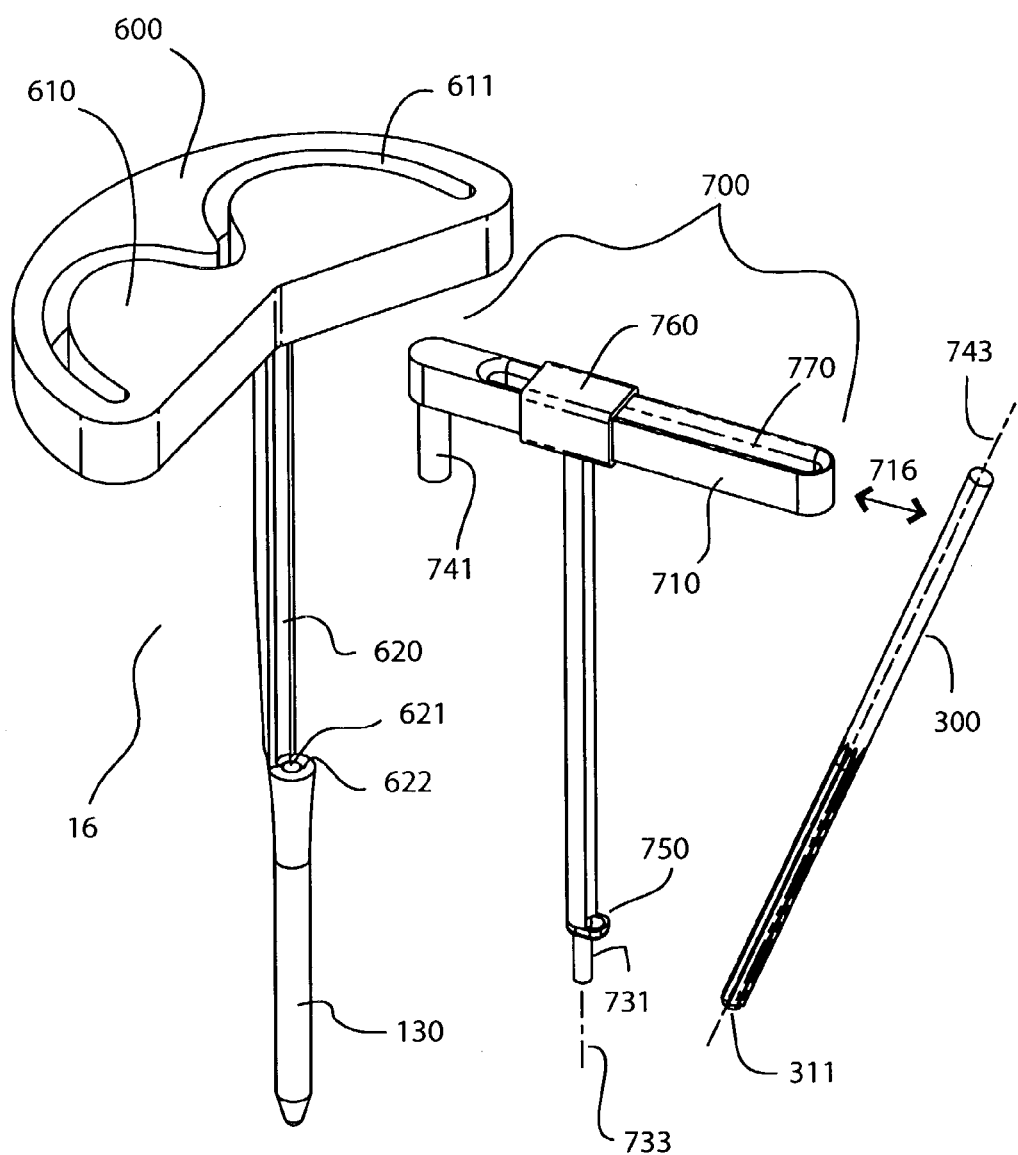
FIG. 16 is an exploded view the bone milling instrument assembly of FIG. 15, showing the guide body, mill guide, and bone cutting mill.

A fifth embodiment of the milling guide instrument 16 is shown in FIGS. 15 and 16. This is a mill guide instrument 16 that has similar subassemblies as the previously described embodiments; a two-dimensional guide body 600, a two-dimensional mill guide 700 and a mill 300.

As described with previous embodiments, this two-dimensional guide body 600 has three main sections that are shown in FIG. 15. These three main sections are a distal stem 130, a guide frame 620, and a template section 611.

Similar to the function of the guide bodies of the other embodiments, the two-dimensional guide body 600 of the embodiment shown in FIGS. 15 and 16 are designed to confine the movement of the mill 300 to a path that is dictated by the two-dimensional template surface 611 and the movement allowed by the two-dimensional guide body 600. The movement of the mill 300 with respect to the two-dimensional mill guide 700 in this two-dimensional milling instrument 16 is restricted by the slot 770 in the two-dimensional mill guide and the pivot point 750 in the mill guide 700. The distal end 311 of the mill 300 is received to rotate about this pivot point 750.

When the stylus 741 of the mill guide 700 follows the path 611 in the template 610, the mill 300 is constrained to movement along a direction 716 that is in line with the mill guide axis 733 and the point that the stylus is along the two-dimensional template surface. This keeps the mill 300 following the preferred mill path 24 that is a result of the geometry of the template guide surface 611.

The fifth embodiment of the bone milling instrument assembly 16 creates a cutting path that is along the longitudinal cutting flutes 316 on the mill 300. The cutting path is always pivoting around the receptor 750 in the mill guide 700.

In this fifth embodiment of the bone milling instrument assembly 16, the slot 770 is oriented longitudinally in a cross-bar 710. A slider joint 760 allows the crossbar 710 to slide perpendicularly through the mill guide axis 733 at the opposite end of the joint shaft 731, which is at the distal end of the mill guide 700 as shown in FIG. 16.

Figure 17:
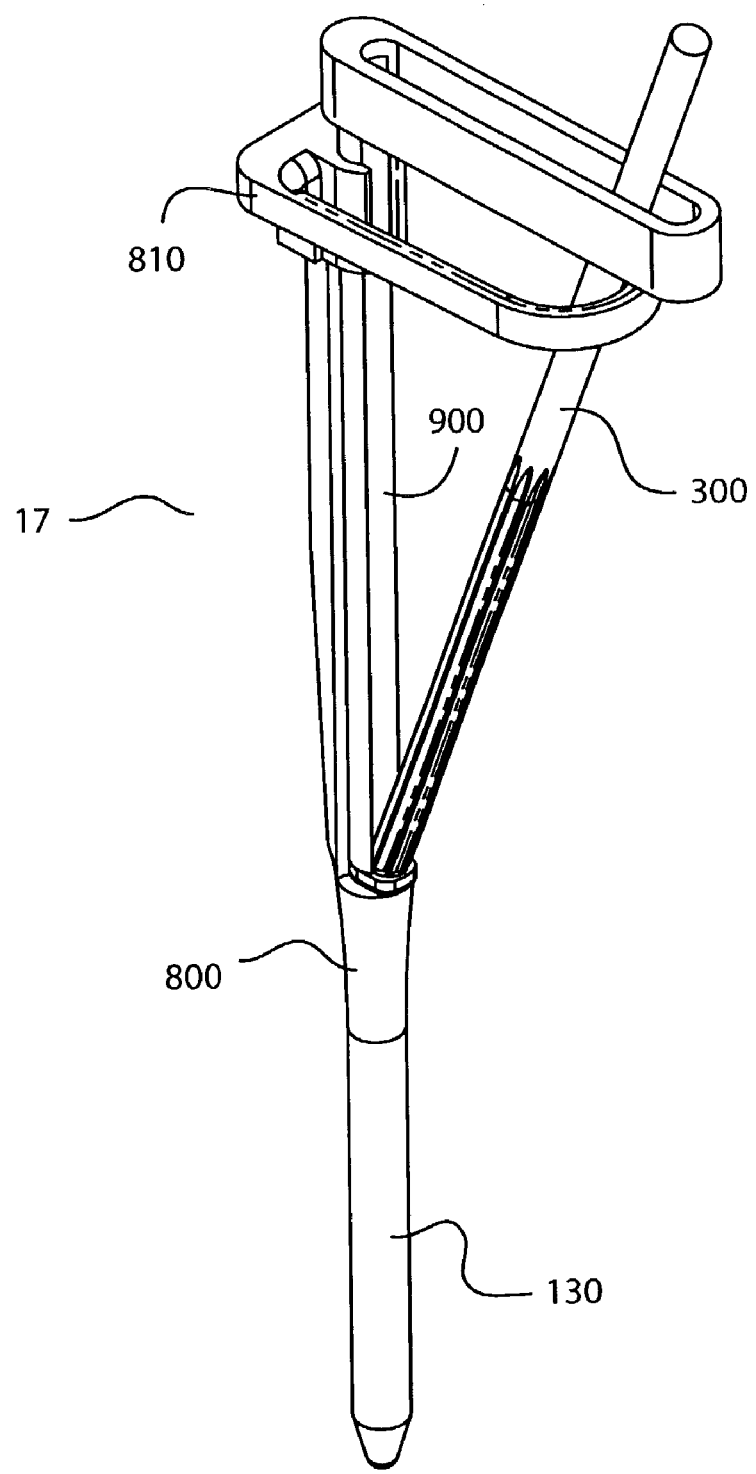
FIG. 17 is a perspective view of a sixth embodiment of a bone milling instrument assembly using a two-dimensional template and a mill guide with a slot to collaboratively guide the mill.
Figure 18:
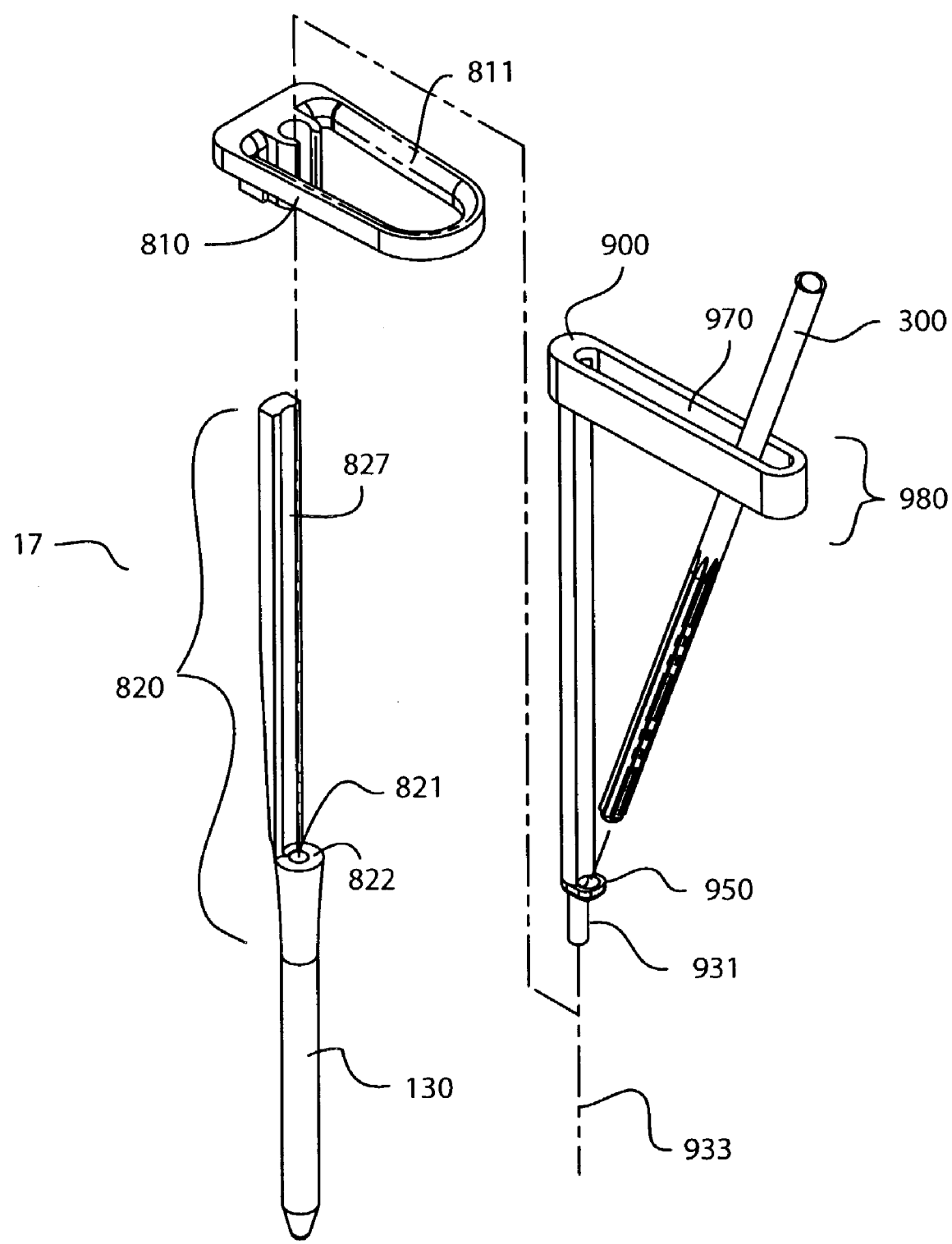
FIG. 18 is an exploded view of the bone milling instrument assembly of FIG. 17, showing the guide body, the template section with a two-dimensional guide surface, the mill guide, and the mill.

In a sixth embodiment of the bone milling instrument assembly 17 shown in FIGS. 17 and 18, the mill 300 also pivots about a receptor 950 in the mill guide 900 and slides within a slot 970 that is within the mill guide proximal section 980. However, in this sixth embodiment of the bone milling instrument assembly 17, the mill guide 900 rotates around the mill guide axis 933. The mill 300 is constrained with respect to the mill frame 800 to within the boundaries defined by the template guide surface 810.

Similar to the other embodiments, a particular template 810 is selected by the surgeon from a range of available templates to provide a preferred cutting surface 21 that best fits the external surface geometry of the prosthesis.

While the present invention has been disclosed in its preferred form, the specific embodiments thereof as disclosed and illustrated herein are not to be considered in a limiting sense, as numerous variations are possible. The invention may be embodied in other specific forms without departing from its spirit or essential characteristics. The described embodiments are to be considered in all respects only as illustrative and not restrictive. No single feature, function, element or property of the disclosed embodiments is essential. The scope of the invention is, therefore, indicated by the appended claims rather than by the foregoing description. The following claims define certain combinations and subcombinations that are regarded as novel and non-obvious. Other combinations and subcombinations of features, functions, elements and/or properties may be claimed through amendment of the present claims or presentation of new claims in this or related applications. Such claims, whether they are broader, narrower or equal in scope to the original claims, are also regarded as included within the subject matter of applicant's invention. All changes that come within the meaning and range of equivalency of the claims are to be embraced within their scope.

What is claimed is:

1. A mill guide instrument for guiding a tissue cutting mill, the mill guide instrument comprising:
    a guide body comprising a distal section adapted to fit into a bore in a bone and a template section having a guide surface; and
    a mill guide selectively mounted on the guide body and adapted to engage the tissue cutting mill, the mill guide comprising a stylus configured to selectively follow the guide surface of the template section such that the mill guide orients the tissue cutting mill towards tissue to be removed from the bone to form a bone cavity;
    wherein the guide surface is shaped to permit the tissue cutting mill to follow a three-dimensional cutting path.

2. A mill guide instrument as in claim 1, wherein the guide surface of the template section comprises a three-dimensional guide surface.

3. A mill guide instrument as in claim 1, wherein the guide surface of the template section comprises a two-dimensional guide surface.

4. A mill guide instrument as in claim 1, 2, or 3 wherein the guide body further comprises a guide body frame and the template section is removably connectable to the guide body frame.

5. A mill guide instrument as in claim 1, wherein the mill guide comprises a follower that selectively moves axially during operation.

6. A mill guide instrument as in claim 1, wherein the guide body comprises a guide body frame.

7. A mill guide instrument as in claim 6, wherein the guide body comprises a distal stem that is removably connected to the guide body frame.

8. A mill guide instrument as in claim 7 further comprising a plurality of distal stems that are removably connectable to the guide body frame, the distal stem begin selected from the plurality of distal stems.

9. A mill guide instrument as in claim 1, wherein the mill guide comprises:
    a sleeve attached to the stylus;
    a pivot guide rotationally connected to the sleeve about a first axis of rotation; and
    an arbor rigidly connected to the pivot guide, the arbor being rotationally connected to the guide body about a second axis of rotation.

10. A mill guide instrument as in claim 9, wherein a first axis of rotation is substantially perpendicular to the second axis of rotation.

11. A mill guide instrument as in claim 9, wherein a long axis of the stylus is substantially perpendicular to a long axis of the sleeve.

12. A mill guide instrument as in claim 11, wherein the sleeve is slidably connected to the pivot guide along the longitudinal axis of the sleeve.

13. A mill guide instrument for cutting a cavity in bone comprising:
    a guide body comprising a distal section dimensioned to fit into a bore in a bone and a template section having a guide surface with a non-circular cross sectional shape;
    a mill guide rotationally connected to the guide body at a pivot guide positioned to be outside the cavity during removal of tissue from the bone, the mill guide comprising a stylus and a sleeve;
    a mill slidably received within the sleeve, the mill having a proximal section, distal section and a shaft extending therebetween, the mill being oriented toward the tissue to be removed when the stylus selectively follows the guide surface of the template section.

14. A mill guide instrument of claim 13, wherein when the distal section of the mill has cutting flutes formed thereat.

15. A milling instrument of claim 13, further comprising a driver which drives the mill in an oscillatory-rotary motion, the oscillatory-rotary motion being essentially alternating clockwise and counterclockwise rotary motion with respect to a longitudinal axis of the mill.

16. A milling instrument of claim 13, wherein the distal section of the mill has cutting flutes that cut engaged tissue when the mill is driven in an oscillatory-oscillatory motion.

17. A milling instrument of claim 13, wherein the mill is driven by longitudinal-vibratory motion, the longitudinal-vibratory motion being essentially alternating forward and reverse longitudinal motion with respect to a longitudinal axis of the mill.

18. A milling instrument of claim 17, wherein the distal cutting section of the mill has cutting flutes that cut engaged tissue when the mill is driven in a longitudinal-vibratory motion.

19. A mill guiding instrument for cutting a cavity in bone, comprising:
    a support frame having a distal portion adapted to be received within a bore in the bone;
    a mill guide connected to the support frame and having a stylus;
    a mill adapted to cut tissue and adapted to rotate within and relative to the mill guide; and
    a template connected to the support frame and having a guide surface configured such that tracing the template with the stylus, causes the mill guide to position the mill such that a desired cavity is cut into the bone wherein the guide surface is shaped to permit the tissue cutting mill to follow a three-dimensional cutting path.

20. A mill guide instrument for cutting a cavity in bone as in claim 19 wherein the template section is removably connected to the guide frame.

* * * * *

UNITED STATES PATENT AND TRADEMARK OFFICE
CERTIFICATE OF CORRECTION

PATENT NO.         : 7,090,677 B2
APPLICATION NO. : 10/366300
DATED                : August 15, 2006
INVENTOR(S)       : T. Wade Fallin et al.

It is certified that error appears in the above-identified patent and that said Letters Patent is hereby corrected as shown below:

- Column 3. Line 19 (summary of invention)
ADD --of-- after "external geometry"

- Column 5. Line 1 (description of drawings)
delete "a" and ADD --an-- before "exploded view of the bone"

- Column 10. Line 67 (detailed description)
delete "releasabily" and ADD --releasably--

- Column 11. Line 17 (detailed description)
delete "he" and ADD --the-- after "the groove 1160 at"

- Column 11. Line 36 (detailed description)
delete "forth" and ADD --fourth--

- Column 11. Line 40 (detailed description)
delete "these" and ADD --the-- after "The separation of"

- Column 12. Line 19 (detailed description)
delete "are" and ADD --is-- after "shown in FIGS. 15 and 16"

- Column 13. Line 49 (claim 8)
delete "begin" and ADD --being--

- Column 14. Line 23 (claim 14)
delete "when" after "wherein"

- Colum 14. Line 32 (claim 16)
delete "oscillatory-oscillatory" and ADD --oscillatory-rotary--

UNITED STATES PATENT AND TRADEMARK OFFICE
CERTIFICATE OF CORRECTION

PATENT NO.       : 7,090,677 B2
APPLICATION NO.  : 10/366300
DATED            : August 15, 2006
INVENTOR(S)      : T. Wade Fallin et al.

It is certified that error appears in the above-identified patent and that said Letters Patent is hereby corrected as shown below:

- Column 14. Line 53 (claim 19)
delete "," following "tracing the template with the stylus"

Signed and Sealed this

Twentieth Day of February, 2007

JON W. DUDAS
*Director of the United States Patent and Trademark Office*

UNITED STATES PATENT AND TRADEMARK OFFICE
CERTIFICATE OF CORRECTION

PATENT NO. : 7,090,677 B2
APPLICATION NO. : 10/366300
DATED : August 15, 2006
INVENTOR(S) : T. Wade Fallin et al.

It is certified that error appears in the above-identified patent and that said Letters Patent is hereby corrected as shown below:

Column 1. Line 17.
DELETE "-" that appears in front of "correspondingly"

Column 4. Line 7.
DELETE "threeonal dimensional" and ADD --three-dimensional--

Column 4. Line 23.
DELETE "a" that precedes "anteromedial perspective view" and ADD --an-- in its place Column 7. Line 13.
DELETE "mills" and ADD --mill--

Column 7. Line 42 and 56
DELETE "220" that follows "arbor boss" and ADD --221--

Column 7. Line 60.
DELETE "is" that follows "rotational freedom"

Column 10. Line 58.
DELETE "axis" and ADD --axes--

Column 10. Line 61.
DELETE "joins" and ADD --joints--

UNITED STATES PATENT AND TRADEMARK OFFICE
CERTIFICATE OF CORRECTION

PATENT NO. : 7,090,677 B2
APPLICATION NO. : 10/366300
DATED : August 15, 2006
INVENTOR(S) : T. Wade Fallin et al.

It is certified that error appears in the above-identified patent and that said Letters Patent is hereby corrected as shown below:

Column 11. Line 10.
DELETE "," after "FIGS. 9" and ADD --,-- after "FIGS. 9 and 10"

Signed and Sealed this

Sixth Day of March, 2007

JON W. DUDAS
*Director of the United States Patent and Trademark Office*